United States Patent
Rosenthal et al.

(10) Patent No.: US 11,241,306 B2
(45) Date of Patent: *Feb. 8, 2022

(54) NASAL IMPLANTS, DELIVERY TOOLS, SYSTEMS, AND METHODS OF USE

(71) Applicant: Spirox, Inc., Maple Grove, MN (US)

(72) Inventors: Michael H. Rosenthal, Maple Grove, MN (US); Scott Jeffrey Baron, Maple Grove, MN (US); Donald A. Gonzales, Maple Grove, MN (US); Piyush Arora, Maple Grove, MN (US); Michael S. Mirizzi, Maple Grove, MN (US); Pankaj Rathi, Maple Grove, MN (US); Christopher Marquis, Maple Grove, MN (US)

(73) Assignee: Spirox, Inc., Maple Grove, MN (US)

( * ) Notice: Subject to any disclaimer, the term of this patent is extended or adjusted under 35 U.S.C. 154(b) by 66 days.

This patent is subject to a terminal disclaimer.

(21) Appl. No.: 16/604,490

(22) PCT Filed: Apr. 13, 2018

(86) PCT No.: PCT/US2018/027560
§ 371 (c)(1),
(2) Date: Oct. 10, 2019

(87) PCT Pub. No.: WO2018/191659
PCT Pub. Date: Oct. 18, 2018

(65) Prior Publication Data
US 2020/0054446 A1     Feb. 20, 2020

Related U.S. Application Data

(60) Provisional application No. 62/485,309, filed on Apr. 13, 2017.

(51) Int. Cl.
*A61F 2/18* (2006.01)
*A61B 17/34* (2006.01)
*A61L 27/58* (2006.01)
*A61B 17/24* (2006.01)

(52) U.S. Cl.
CPC .......... *A61F 2/186* (2013.01); *A61B 17/3468* (2013.01); *A61L 27/58* (2013.01);
(Continued)

(58) Field of Classification Search
CPC .............. A61F 2/186; A61F 2220/0016; A61F 2210/0004; A61L 27/58; A61M 2210/0618; A61B 2017/246; A61B 17/3468
See application file for complete search history.

(56) References Cited

U.S. PATENT DOCUMENTS 6,322,590 B1    11/2001  Sillers et al.
2007/0270899 A1 11/2007  aWengen et al.
(Continued)

FOREIGN PATENT DOCUMENTS

DE         20307058 U1    8/2003
DE   10 2006 023 058 B3  10/2007
(Continued)

OTHER PUBLICATIONS

International Search Report dated Sep. 18, 2018, issued in connection with International Application No. PCT/US2018/027560, filed on Apr. 13, 2018, 4 pages.
(Continued)

*Primary Examiner* — Dinah Baria
(74) *Attorney, Agent, or Firm* — McDonnell Boehnen Hulbert & Berghoff LLP

(57) ABSTRACT

Nasal implants are provided that have a planar type profile with open spaces through portions of the planar type profile. The nasal implant can be compressible along one or more
(Continued)

dimensions of the nasal implant, such as the width and length of the planar type profile. Delivery tools for deploying the nasal implants within the nasal tissue are also provided. Methods for deploying the nasal implants within the nasal tissue of the patient are also provided.

16 Claims, 33 Drawing Sheets

(52) U.S. Cl.
CPC . *A61B 2017/246* (2013.01); *A61F 2210/0004* (2013.01); *A61F 2220/0016* (2013.01); *A61M 2210/0618* (2013.01)

(56) References Cited

U.S. PATENT DOCUMENTS

| | | |
|---|---|---|
| 2011/0125091 A1 | 5/2011 | Abbate |
| 2011/0251634 A1 | 10/2011 | Gonzales et al. |
| 2012/0078367 A1 | 3/2012 | Hristov et al. |
| 2003/0317540 | 11/2013 | Hristov et al. |
| 2013/0317540 A1 | 11/2013 | Hristov et al. |
| 2014/0243975 A1* | 8/2014 | Di ................. A61B 17/3468 623/10 |
| 2016/0058556 A1 | 3/2016 | Rosenthal et al. |
| 2017/0105836 A1 | 4/2017 | Baron et al. |

FOREIGN PATENT DOCUMENTS

| | | |
|---|---|---|
| WO | 2011/119084 A1 | 9/2011 |
| WO | 2015/192162 A1 | 12/2015 |

OTHER PUBLICATIONS

Written Opinion dated Sep. 18, 2018, issued in connection with International Application No. PCT/US2018/027560, filed on Apr. 13, 2018, 10 pages.

* cited by examiner

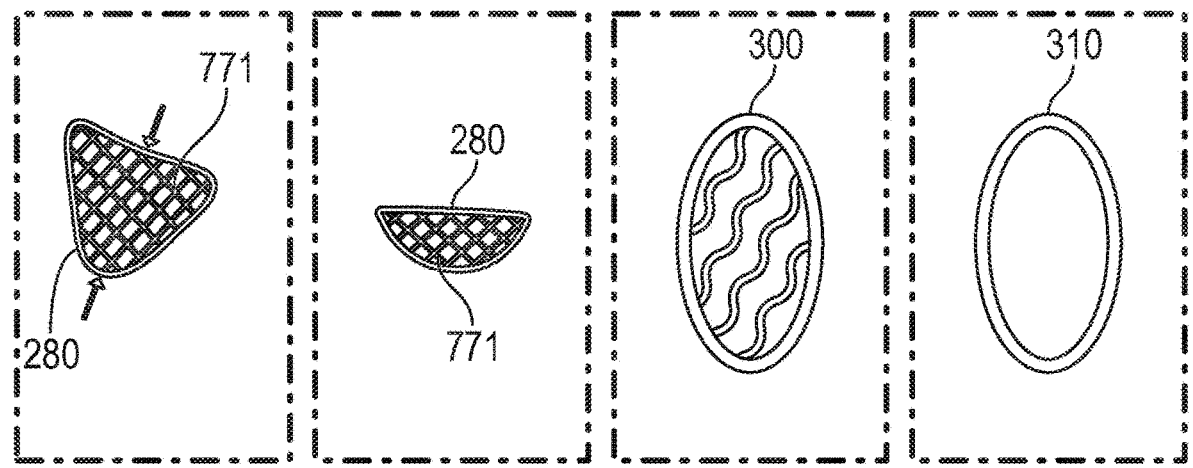
FIG. 7A  FIG. 7B  FIG. 7C  FIG. 7D
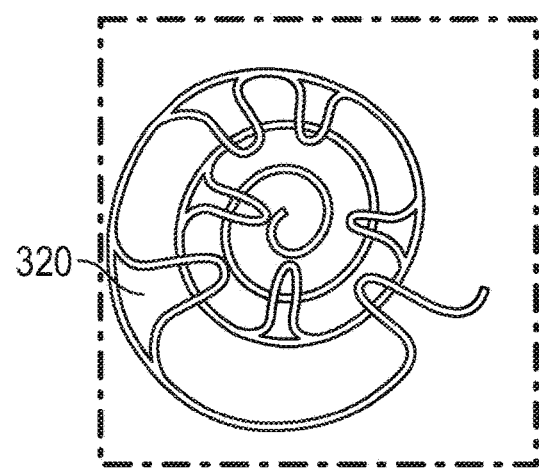 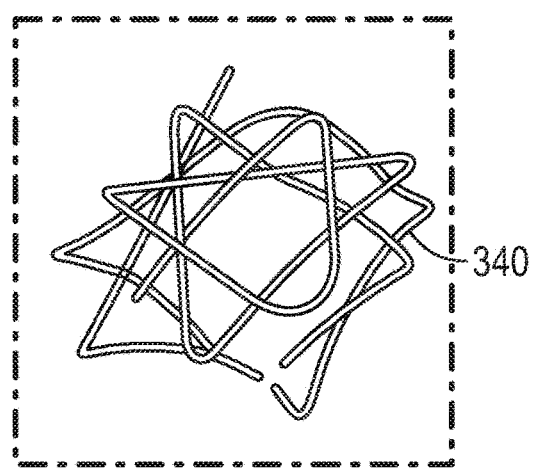
FIG. 7E  FIG. 7F

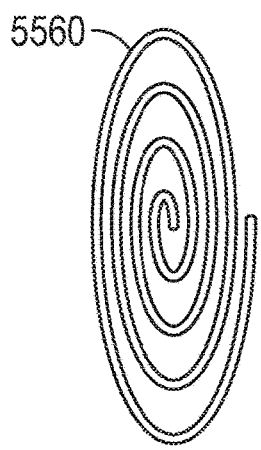
FIG. 8A
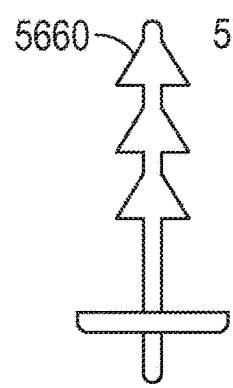
FIG. 8B
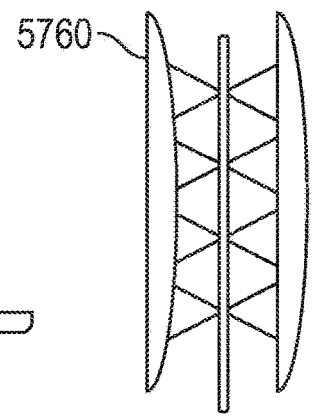
FIG. 8C
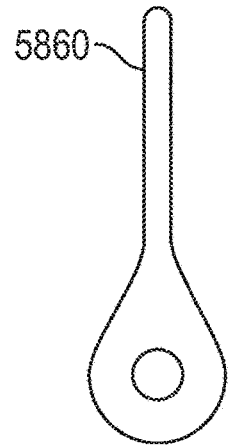
FIG. 8D
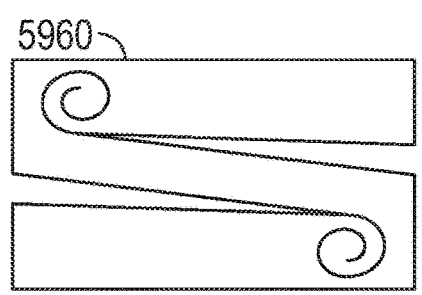
FIG. 8E
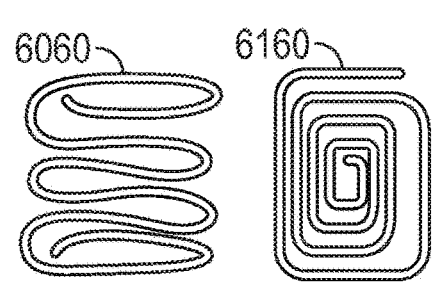
FIG. 8F
FIG. 8G
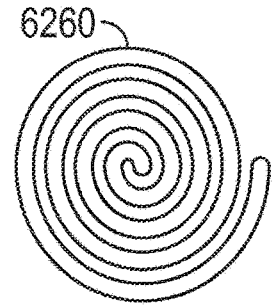
FIG. 8H
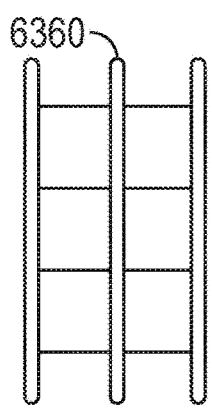
FIG. 8I
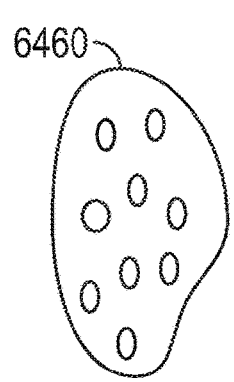
FIG. 8J
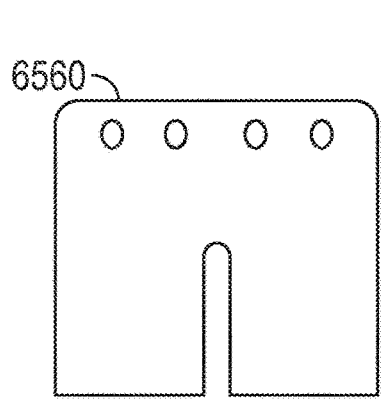
FIG. 8K

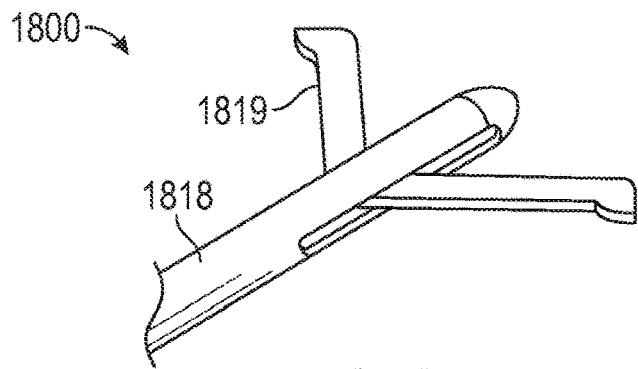
FIG. 18
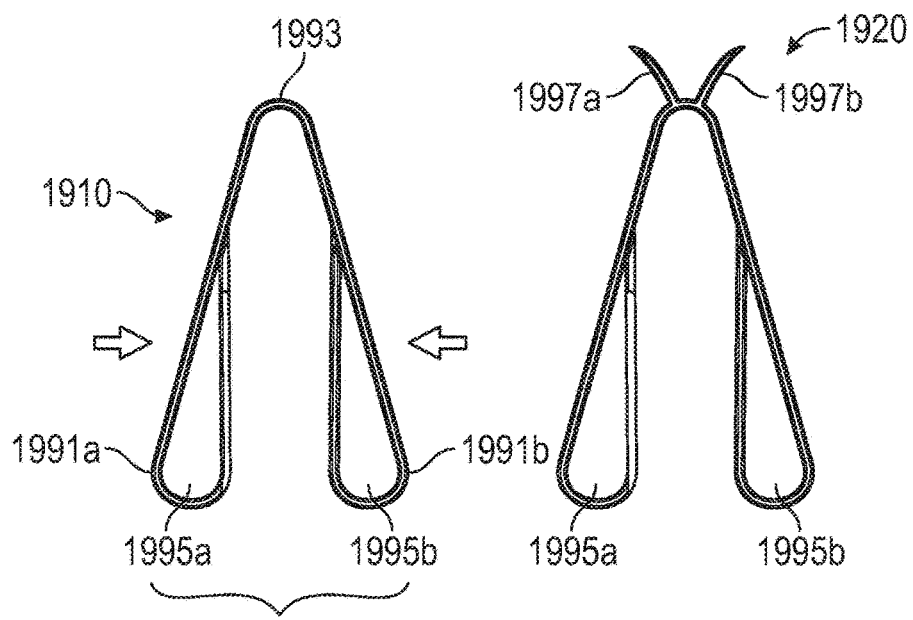
FIG. 19A
FIG. 19B
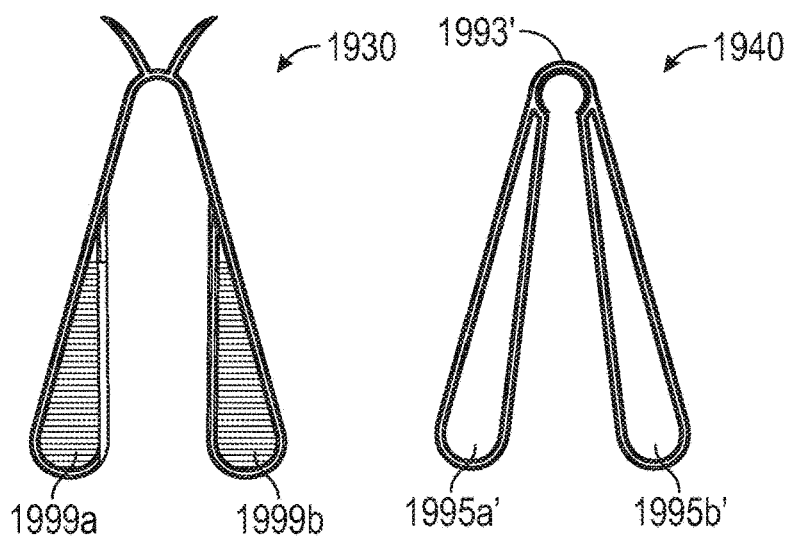
FIG. 19C
FIG. 19D

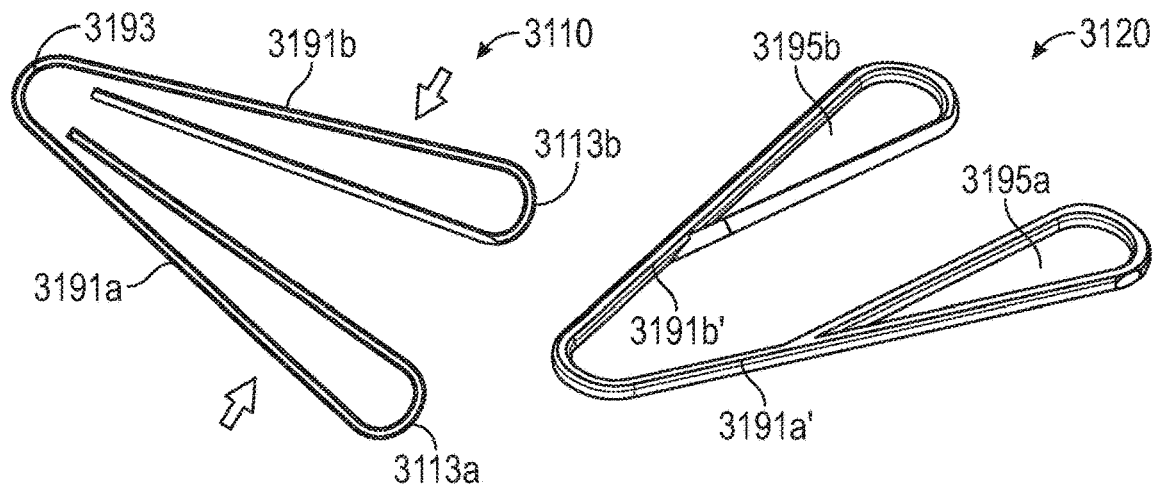
FIG. 31A
FIG. 31B
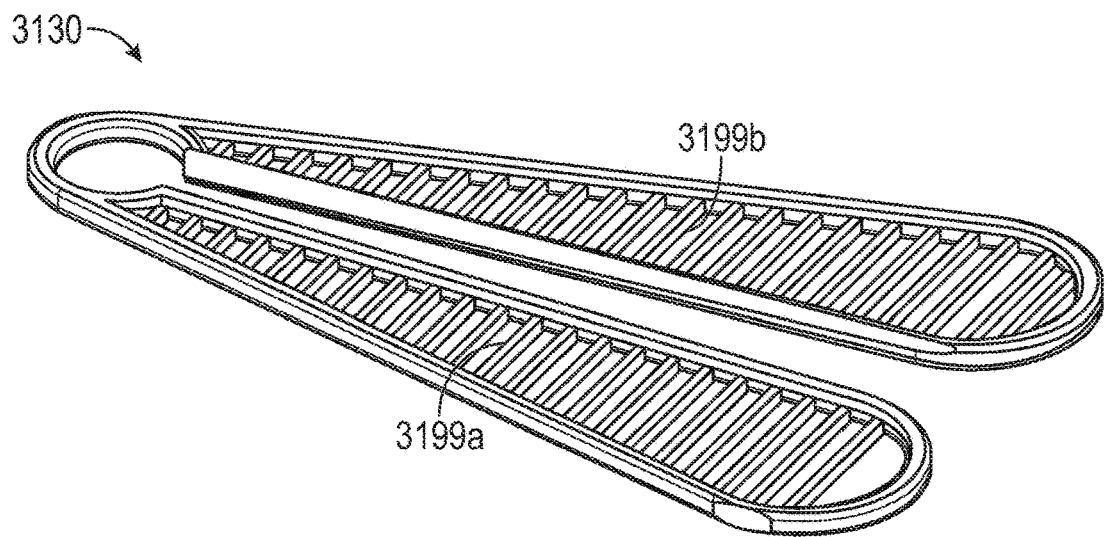
FIG. 31C
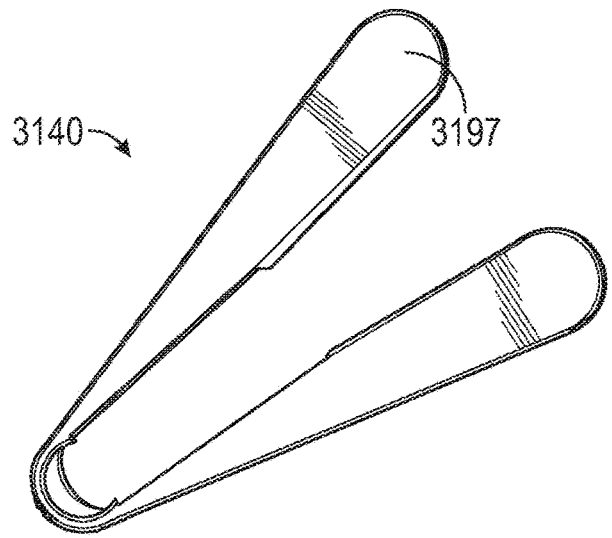
FIG. 31D

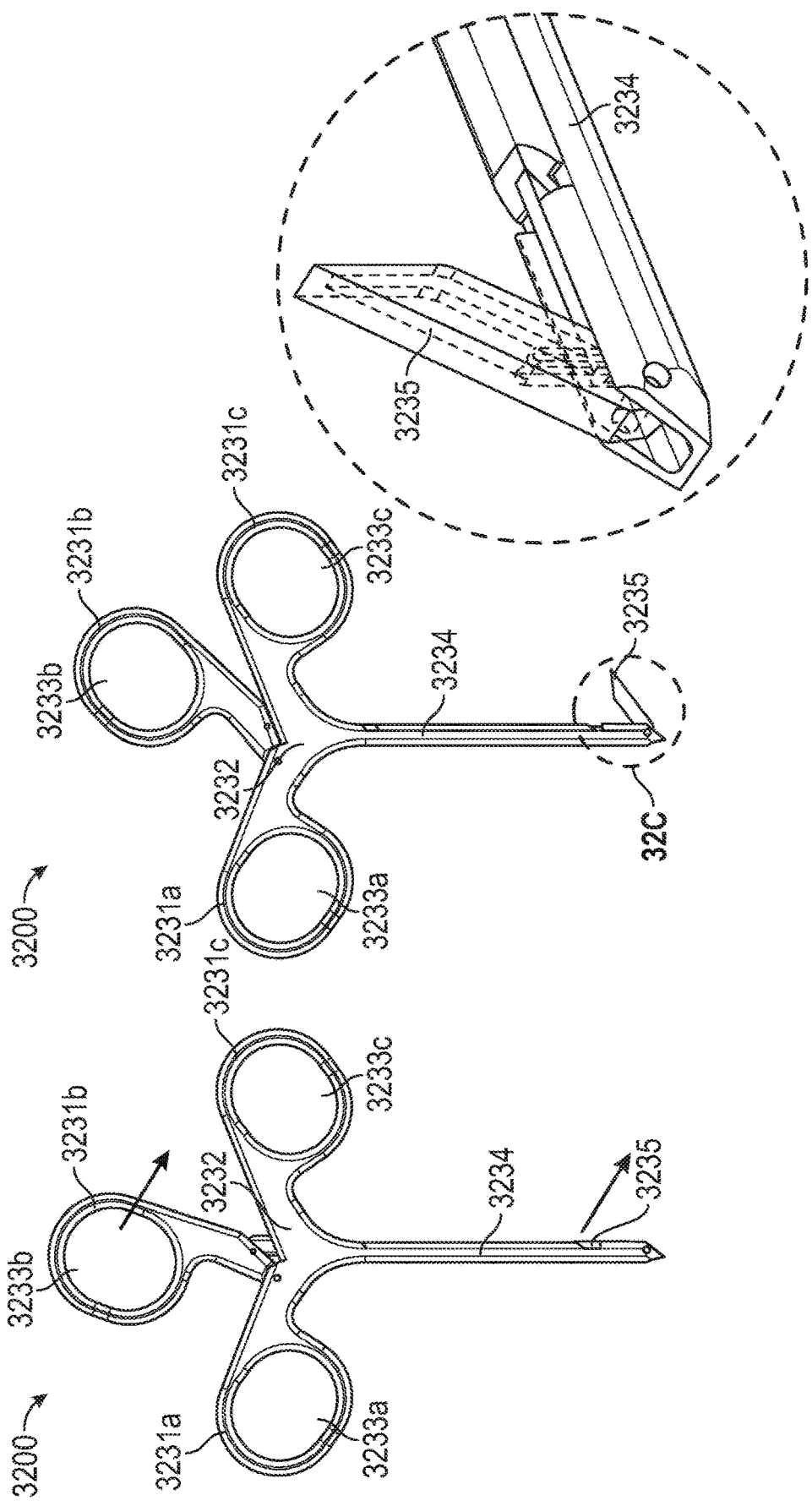

NASAL IMPLANTS, DELIVERY TOOLS, SYSTEMS, AND METHODS OF USE

CROSS REFERENCE TO RELATED APPLICATIONS

This application claims priority to U.S. Provisional Application No. 62/485,309, filed Apr. 13, 2017, titled "NASAL IMPLANTS, DELIVERY TOOLS, SYSTEMS, AND METHODS OF USE", the entirety of which is incorporated by reference herein.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are implants for placing in a body, tools for delivering the implants, and systems and methods for using implants and tools for placing in a body. More particularly, described herein are nasal implants, tools for delivering nasal implants, and systems and methods for using such implants and tools.

BACKGROUND

Nasal Valve Collapse (NVC) and Lateral Wall Insufficiency (LWI) are used to describe a nasal tissue mechanical deficiency and/or nasal airway cross-sectional area contribution to limit airflow through the nasal valve region. Dynamic NVC is a significant contributor to Nasal Airway Obstruction (NAO), a condition effecting tens of millions of individuals.

There is a need for a device and delivery system to improve the shape and/or structural integrity of the nasal lateral wall in the area of the upper and lower lateral cartilage to help combat NVC and LWI. The upper and lower later cartilages are positioned to support the lateral wall upon inhalation, but may be weak due to causes such as aging, trauma, and native anatomy. These structures may have also been manipulated and compromised from previous surgeries or removed entirely, causing a weak nasal lateral wall prone to collapse during inhalation.

Surgical solutions to NVC and LWI have been previously described, including placement of alar batten grafts and spreader grafts that utilize autologous grafts harvested from the nasal septum, ear, or ribs. Surgical techniques, such as suture suspension, have also been utilized that combine device and invasive surgical techniques to provide support to the lateral wall. These surgeries are complicated and invasive, have a significant cosmetic impact, and are highly dependent on the skill of the physician. Robust mechanical implants have also been developed to alleviate NVC and LWI. These implants include titanium or alternative metal implants that saddle the bridge of the nose and span the lateral wall, permanent synthetic polymer implants that are pre-shaped similar to what would be required of an alar batten graft, and shapeable absorbable or permanent sheet products that may be configured by the physician as temporary supporting or splinting structure for reshaped or repositioned cartilage, or as pre shaped grafts. These options have shown promise, but have often resulted in tissue rejection of the synthetic materials and subsequent extrusions. Complaints of undesirable cosmetic effects, foreign body sensation, pain, and discomfort have all also been reported.

U.S. Patent Publication No. 2016-0058556 describes a minimally invasive option to address the above issues, including a method for delivering a rod shaped implant device within the lateral wall using a needle based delivery device approach. This implant supports the lateral cartilage by bridging the cartilage and boney structures of the local lateral nasal anatomy. This solution provides significant improvement, and the synthetic absorbable polymer structure can be reactive in the surrounding tissues when compared to previous non-autologous synthetic implant options like porous polyethylene, silicone, PGA, PDS, etc. The nasal implants in U.S. Patent Publication No. 2016-0058556 are applicable to many anatomies, but there may be some individuals that need a more robust mechanical solution. Patients that may need a more robust mechanical solution include those with little to no cartilage to support. They may also include patients with narrow airways requiring no dynamic motion or nearly no dynamic motion of the lateral wall upon inspiration.

There is thus a need for a more robust implant for supporting the lateral wall. There is also a need for improved delivery systems for delivering nasal implants as well as improved methods for delivering the nasal implants.

SUMMARY OF THE DISCLOSURE

The present invention relates to nasal implants that can be used to support portions of a nasal anatomy of a patient. Also, described herein are delivery tools and methods of delivering the nasal implants described herein to support nasal tissue.

In general, in one embodiment, a nasal implant includes a first portion and a second portion. The first portion and the second portion together form a profile of the implant. The nasal implant is flexible at discrete locations along the profile, and the nasal implant as a whole is configured to be rigid along the profile when a force is applied to substantially all of the profile.

This and other embodiments can include one or more of the following features. At least part of the second portion can be spaced away from at least part of the first portion along the profile such that the first portion is compressible relative to the second portion. The nasal implant includes a first plane that can include the first and second portions and a second plane that can be generally perpendicular to the first plane, and the nasal implant can be compressible in the first plane and flexible in the second plane. The profile can be substantially planar. The profile can include a curved planar profile. The profile can be substantially flat. The first and second portions can be substantially equal in size. The first and second portions can be substantially symmetrical. The profile can have a coil configuration. The profile can have a rounded shape. The profile can have an oval shape. The profile can have a circular shape. The profile can have a substantially triangular shape. The first portion can be a first elongate member and the second portion can be a second elongate member, and the first and second elongate members can be connected together at a distal junction and disconnected at a proximal end. The first and second elongate members can be substantially straight. The first and second elongate members each can have one or more loops formed therein. The one or more loops can be filled with a mesh or ribbed material. The first and second elongate members each can have a plurality of ridges extending therearound. The implant can have a width of 3-5 mm, a height of 3 mm or more, and a thickness of 1 mm or less. The nasal implant can be configured to fit between a mucosa and a dermis of a nasal lateral wall. The nasal implant can be configured to fit between the mucosa and a nasal septum. The profile can include a body portion with a plurality of projections that each project from the body portion. The plurality of projections can include three or more projections. A distal end of the implant can include a fork feature thereon. The fork feature can be configured to accept a nasal bone therein. The implant can include at least one open space therein that includes from about 5% to about 20% of a surface area of the profile. The implant can include at least one open space therein that includes about 20% or greater of a surface area of the profile. The profile can have a flexural rigidity of about 2 N*mm2 to about 500 N*mm2. The nasal implant can include a first bioabsorbable material. The nasal implant can consist essentially of the first bioabsorbable material. The nasal implant can include the first bioabsorbable material with a first degradation profile and a second bioabsorbable material with a second degradation profile. The first bioabsorbable material can be polydioxanone. The second bioabsorbable material can be selected from the group consisting of: PLA, PLLA, and PLDLA. The first degradation profile can be about 1 to 6 months. The second degradation profile can be about 18 to 48 months. The implant can include a plurality of flexible struts. The implant can include a mesh material. The implant can include a plurality of coiled loops therein. The implant can include a plurality of looped projections. The implant can include a plurality of perforations therethrough.

In general, in one embodiment, a nasal implant includes a first portion and a second portion. The first portion and the second portion together form a profile of the implant. At least part of the second portion is spaced away from at least part of the first portion along the profile such that the first portion is compressible relative to the second portion, and the nasal implant as a whole is configured to be rigid along the profile when a force is applied to substantially all of the profile.

This and other embodiments can include one or more of the following features. The nasal implant can include a first plane including the first and second portions, and the nasal implant can be compressible in the first plane. The nasal implant can include a second plane that can be generally perpendicular to the first plane, and the nasal implant can be flexible in the second plane. The profile can be substantially planar. The profile can include a curved planar profile. The profile can be substantially flat. The first and second portions can be substantially equal in size. The first and second portions can be substantially symmetrical. The profile can have a coil configuration. The profile can have a rounded shape. The profile can have an oval shape. The profile can have a circular shape. The profile can have a substantially triangular shape. The first portion can be a first elongate member and the second portion can be a second elongate member, and the first and second elongate members can be connected together at a distal junction and disconnected at a proximal end. The first and second elongate members can be substantially straight. The first and second elongate members each can have one or more loops formed therein. The one or more loops can be filled with a mesh or ribbed material. The nasal implant can further include a compressible hinge extending between the first and second elongate members. The implant can have a width of 3-5 mm, a height of 3 mm or more, and a thickness of 1 mm or less. The nasal implant can be configured to fit between a mucosa and a dermis of a nasal lateral wall. The nasal implant can be configured to fit between the mucosa and a nasal septum. The profile can include a body portion with a plurality of projections that each project from the body portion. The plurality of projections can include three or more projections. A distal end of the implant can include a fork feature thereon. The fork feature can be configured to accept a nasal bone therein. The implant can include at least one open space therein that includes from about 5% to about 20% of a surface area of the profile. The implant can include at least one open space therein that includes about 20% or greater of a surface area of the profile. The profile can have a flexural rigidity of about 2 N*mm2 to about 500 N*mm2. The nasal implant can further include a first bioabsorbable material. The nasal implant can consist essentially of the first bioabsorbable material. The nasal implant can include the first bioabsorbable material with a first degradation profile and a second bioabsorbable material with a second degradation profile. The first bioabsorbable material can be polydioxanone. The second bioabsorbable material can be selected from the group consisting of: PLA, PLLA, and PLDLA. The first degradation profile can be about 1 to 6 months. The second degradation profile can be about 18 to 48 months. The nasal implant can be substantially incompressible along a second plane that is perpendicular to a first plane that includes the first and second portions. The first portion and the second portion can be configured to overlap one another when the implant is in a compressed configuration. The first portion and the second portion can be configured to about one another when the implant is in a compressed configuration.

In general, in one embodiment, a delivery tool includes a handle portion with a hand grippable surface, and an elongate member having a proximal end and a distal end. The proximal end engaged with the handle portion. The distal end includes an implant chamber adapted to hold any of the nasal implants described herein and an opening adapted to eject the nasal implant from the implant chamber.

This and other embodiments can include one or more of the following features. The opening can be at the distal end of the elongate member and can include a central axis of the elongate member. The opening can be adjacent to the distal end of the elongate member and can be orthogonal to a central axis of the elongate member. The delivery tool can further include a cutting surface on the distal end of the elongate member. The cutting surface can be at a distal most end of the elongate member. The cutting surface can include a scissor element with blades at lateral edges of the scissors such that the lateral edges are adapted to make a planar opening in the nasal tissue when the lateral edges move away from a central axis of the elongate member.

In general, in one embodiment, a method for delivering a nasal implant includes creating a pocket within a nasal tissue of a patient and placing a nasal implant as described herein within the pocket.

This and other embodiments can include one or more of the following features. The pocket within the nasal tissue of the patient can be between a mucosa and a dermis. The pocket within the nasal tissue of the patient can be between a mucosa and a nasal septum. The pocket within the nasal tissue of the patient can be between a dermis and a lateral cartilage. The method can further include suturing the nasal tissue after placing the nasal implant. The method can further include applying energy to a portion of the nasal tissue adjacent to the pocket. The method can further include carrying the nasal implant with any of the delivery tools of followed by placing the nasal implant by passing the nasal implant through the opening in the elongate member of the delivery tool. Carrying can include holding the nasal implant with a compressed length and/or width.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 7A-7F illustrate exemplary nasal implants.

FIGS. 8A-8M illustrate exemplary nasal implants.

FIG. 18 shows an exemplary tool configured to make a pocket in the nasal anatomy.

FIGS. 19A-19D show exemplary nasal implants having two wide legs hinged together.

FIGS. 31A-31D show exemplary nasal implants.

FIGS. 32A-32C show an exemplary tool configured to make a pocket in the nasal anatomy.

FIG. 44A shows a front view of the fork features while FIG. 44B shows a side view of the fork features.

FIG. 45A shows a front view of the fork features while FIG. 45B shows a side view of the fork features.

FIG. 47A shows a front view of the fork features while FIG. 47B shows a side view of the fork features.

DETAILED DESCRIPTION

A variety of nasal implants, delivery tools, and methods for delivering the nasal implants are described herein. The nasal implants described herein can advantageously provide reliable and safe solutions to patients with NVC or LWI. Further, the nasal implants can advantageously cause little to no impact on the overall cosmetics of the nose. The delivery devices and methods described herein can also provide easier delivery methods and less invasive delivery of the implants. The nasal implants, delivery tools, and methods described herein may advantageously be used in either operating room or office procedures using either general or local anesthesia.

Figure 1:
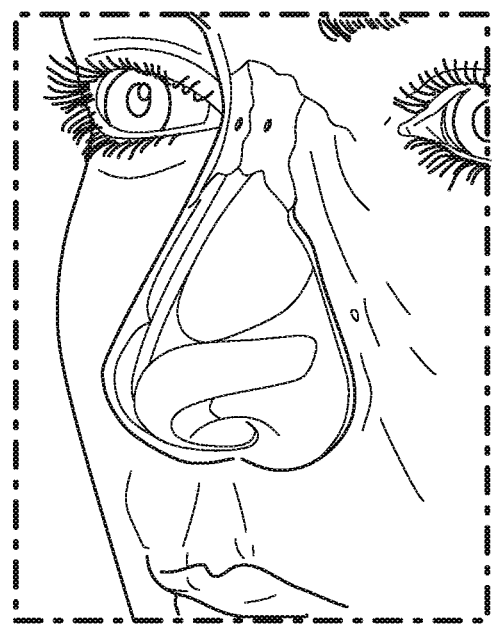
FIG. 1 illustrates the nasal anatomy.
Figure 2A:
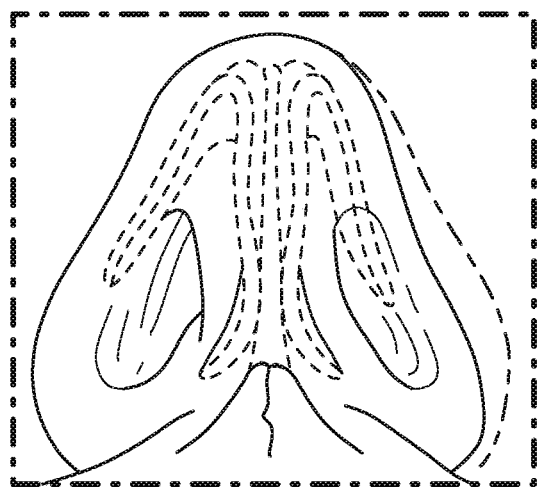
FIGS. 2A-2B illustrates views of a collapsed nasal valve.
Figure 2B:
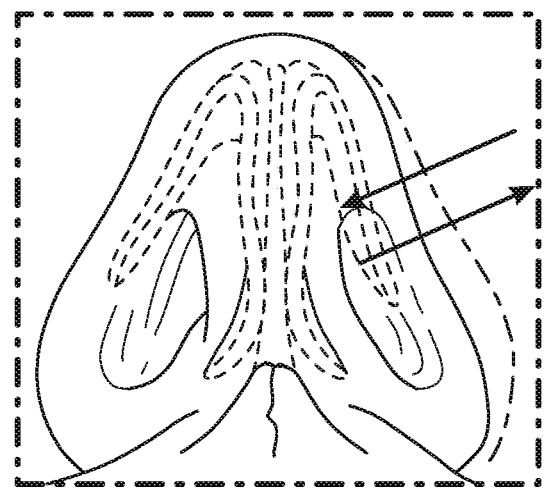

FIG. 1 is an isometric view of the nasal anatomy with the dermis removed. FIGS. 2A-2B illustrate a bottom view of the nose with the nostril on the right side showing some nasal collapse during inhalation as compared to the dotted line showing the nasal structure before/after inhalation. The collapsed nasal valve shown in FIGS. 2A-2B can be caused be a variety of factors that can contribute to the decrease in the cross-sectional area of the nasal valve during inhalation and the negative pressure created with the nasal airway during inhalation. Nasal implants, as described herein, can help correct for such nasal valve collapse. For example, nasal implants can provide broad support of the nasal lateral wall, specifically in the most mobile or flexible anatomy of the nose, in a configuration that may be preferentially flexible to accommodate natural nasal manipulation but prevent internal medial collapse of the nasal wall upon inspiration.

The implants described herein can have sufficient flexibility to allow for patient comfort during natural facial movements or manual nasal manipulation, particularly in the cephalic/compressive direction of the anatomy (e.g. nose wiping, blowing and/or cleaning). The flexibility of the implants described herein can also allow for a natural static curvature to be imparted by the surrounding natural anatomical geometry but also be rigid enough to prevent lateral wall collapse imparted during inhalation. The implants described herein may be capable of flexing laterally (outward) from their natural position while being incapable of flexing, or significantly less flexible, in the medial direction (direction of nasal collapse). The implants described herein may further be maximally rigid enough to physically change the shape of the nose in the static and dynamic inhalation states or minimally rigid enough to minimize nasal valve collapse in the dynamic inhalation state.

The implants described herein can be positioned in a variety of orientations relative to the targeted nasal anatomy. For example, the implants may be configured to be positioned adjacent to the upper and/or lower lateral cartilage and/or maxilla/nasal bone, such as medial or lateral to the cartilaginous structures and bone. The implants may also be positioned in the lateral wall in the typical position of the upper and/or lower lateral nasal cartilage, particularly in instances where these cartilaginous structures are not present, such as in post trauma or post-surgery patients. The implants may span a significant region of the lateral wall, potentially forming a substantially triangular geometry with an outer perimeter defined by the nasal dorsum, maxilla/nasal bone and alar rim, as shown by exemplary implants 100, 120 of FIGS. 3A-3B. The implants may span from the maxilla bone to the nasal dorsum in order to facilitate rigid support of the implants at the contacting points. The implants may span a smaller region of the lateral wall, such as that defined by what would be required to span the margin of the upper and lower lateral cartilage alone or bridge the lateral maxilla bone to one or both of the lower lateral cartilage and/or upper lateral cartilage.

A variety of nasal implant configurations are described herein. In an exemplary embodiment, the nasal implant can have a profile formed by a first side of the nasal implant. The profile can have a first length and a first width. The implant can include a second side opposing the first side with the profile including the second side. The profile can include at least one open space between the first side and the second side. The implant can have a thickness between the first side and the second side. The first length, first width, and thickness between the first side and the second side can be configured such that the nasal implant fits within a nasal tissue of a patient. The nasal implant can be flexible along the profile. The nasal implant can be preferentially compressible and preferentially flexible. The nasal implant can include a parallel plane generally parallel to the first and second sides and a perpendicular plane generally perpendicular to the first and second sides. The nasal implant can compressible in the perpendicular plane and flexible in the parallel plane. The nasal implant can be compressible along the first length and the first width.

In some embodiments, the first and second sides are roughly the same size. In some embodiments, the first and second sides are substantially symmetrical. In some embodiments, the first and second sides are asymmetrical. The first length, first width, and thickness between the first side and the second side can be configured such that the nasal implant or a portion of the nasal implant fits between a mucosa and a dermis of the nasal lateral wall, such as medial or lateral to the lateral cartilage structure. The first length, first width, and thickness between the first side and the second side can be configured such that the nasal implant fits between a mucosa and the nasal septum of the nasal tissue. The first length, first width, and thickness between the first side and the second side can be configured such that the nasal implant fits between a mucosa and a dermis of the nasal lateral wall. In some embodiments, the nasal implant is not substantially compressible along the thickness between the first side and the second side. In other embodiments, the nasal implant can be compressible along the thickness.

The nasal implants described herein can include a variety of different profiles, shapes, and configurations. In some embodiments, the profile of the nasal implant is substantially planar. In some embodiments, the profile is substantially flat. For example, the flat profile can include a spiral configuration, such as an oval shaped spiral configuration, or a triangular shape with an open interior. As another example, the flat profile can include a body portion with a plurality of projections that each project from the body portion. In some implementations, the plurality of projections can include three or more projections, such as four or more projections. In some implementations, the projections have a finger-like configuration. In some embodiments, the profile includes a curved planar profile. In some embodiments, the profile has a coil configuration. In some embodiments, the profile has a rounded shape. In some embodiments, the profile has an oval shape. In some embodiments, the profile has a circular shape. Additional profiles are described herein and shown in the figures.

In some embodiments, the implants described herein can be bioabsorbable. The material properties of a bioabsorbable implant change over time. Thus, a bioabsorbable implant can be configured to have any of the material properties, such as those described herein, after a period of time in a body or exposure to a body fluid.

In some embodiments, the implants described herein can include a plurality of bioabsorbable materials with different mechanical properties and degradation profiles. For example, a flat profile of the implant can be defined by a first bioabsorbable material forming a structural component of the flat profile and a second bioabsorbable material including projections from the structural component. The first bioabsorbable material can have a first degradation profile, and the second bioabsorbable material can have a second degradation profile. When the nasal implant is initially implanted, the structural component can provide more rigid support to the nasal tissue immediately after implantation, but can degrade faster than the projections. The longer degradation profile can allow the projections to provide support to the nasal tissue after initial healing and the degradation of the structural component. In some implementations, the projections can have a cilia like configuration. In some implementations, the structural component can have a coil shape. In some implementations, the first degradation profile can be faster than the second degradation profile. In some implementations, the second degradation profile can be faster than the first degradation profile. The degradation profile can be any of the biodegradation profiles described herein.

In some embodiments, the nasal implants described herein include multiple different materials. For example, the nasal implants can include a structural portion that has a longer degradation profile and a higher mechanical strength and a second material that has a faster degradation profile and a lower mechanical strength than the structural material. In one example, the structural portion can be encapsulated by a thin film of the second material. The thin film can secure the structural elements in position with respect to each other. The thin film can make it easier to manipulate the nasal implant while in the delivery tool and during implantation into the nasal tissue. The thin film can improve the ability to fold the implant and compress the implant to allow for insertion through or by the tool. Multiple portions of the implant can be selectively absorbable and can have varying degradation profiles as described herein.

In some embodiments, the profile of the nasal implants described herein can include a plurality of openings to provide for fluid flow or transfer through or across the nasal implant. Allowing fluid flow can promote healthy cartilage tissue, as cartilage does not have a dedicated blood supply and instead relies on blood flow from adjacent tissue. In some embodiments, the nasal implant profile can include a plurality of open spaces between a first side and the second side. The open spaces can be in the form of perforations, pores, large openings, etc. In some examples, there can be one open space between an outer perimeter alone that has appropriate structural integrity. For example, the perimeter can have the shape of a rectangular, circular, oval, triangular configuration and can include a single opening within the interior of the perimeter. In some embodiments, the openings or open spaces can include about 20% or greater of a surface area of the profile. In other embodiments, the openings or open spaces can be as low as 5% of the surface area of the profile of the implant. In some embodiments, the openings or open spaces between the first side and the second side comprise about 5% to about 20% of a surface area of the profile. The size, shape, profile, and configuration of the openings or open spaces can be tailored to provide a desired amount of support to the nasal tissue. In some cases, the nasal implant can be selected such that the size, shape, profile, or configuration of the openings or open spaces can be matched to achieve a desired or predetermined ratio to the lateral wall volume.

The nasal implants described herein can be designed to minimize an inflammatory response and/or a foreign body response to the nasal implant once it has been implanted within the body. For example, the amount of material used in the implant can be reduced to reduce the inflammatory response and/or the foreign body response.

The profile of the nasal implants described herein can have a flexural rigidity of about 2 $N*mm^2$ to about 500 $N*mm^2$. Different regions of the implants may have material properties, such as strength, flexibility, rigidity, or flexural rigidity. In some embodiments, the implants may have one or more material properties chosen to come close to or mimic a material property of a body structure. For example, a flexural rigidity of a nasal implant may be the same as or close to the flexural rigidity of nasal tissue such as cartilage. As described below, some nasal cartilage has a modulus of elasticity measured to be between 5 and 32 MPa. An implant, or a portion of an implant may have a modulus of elasticity between 5 and 32 MPa or greater than 2, 4, 5, 10, 15, 20, 25, 30, 32, 35, 40, or 50 MPa or less than 2, 4, 5, 10, 15, 20, 25, 30, 32, 35, 40, or 50 MPa or any value in between, such as between 2 and 50 Mpa or between 10 and 30 Mpa. A flexural rigidity of some batten grafts formed of septal cartilage has been determined to be between 50 and 130 $N*mm^2$ or 50-140 $N*mm^2$ and the flexural rigidity of an implant or portion of an implant may also be within this range. An implant flexural rigidity may also be greater or less than this. For example, other supporting structures in a body may work with an implant in providing additional support and a lesser amount of support is needed from the implant or supporting tissues may also be weak and greater support may be needed from the implant. An implant or a portion of an implant may have a flexural rigidity of greater than 10 $N*mm^2$, greater than 30 $N*mm^2$, greater than 50 $N*mm^2$, greater than 75 $N*mm^2$, greater than 100 $N*mm^2$, greater than 150 $N*mm^2$, greater than 200 $N*mm^2$, greater than 300 $N*mm^2$, greater than 400 $N*mm^2$ or less than 600 $N*mm^2$, less than 500 $N*mm^2$, less than 420 $N*mm^2$, less than 400 $N*mm^2$, less than 300 $N*mm^2$, less than 200 $N*mm^2$, less than 130 $N*mm^2$, less than 100 $N*mm^2$, or less than 50 $N*mm^2$. For example, an implant or portion of an implant may have a flexural rigidity between 10 to 590 $N*mm^2$; of 30 to 450 $N*mm^2$; of 60-250 $N*mm^2$; of 75-200 $N*mm^2$; 50 and 130 $N*mm^2$; or 9 and 130 $N*mm^2$. In some embodiments, the implant can have a portion with a flexural rigidity that is less than about 130 $N*mm^2$. In some embodiments, the implant can have a portion with a flexural rigidity that is from about 10 to about 130 $N*mm^2$. In some embodiments, the implant can have a portion with a flexural rigidity that is about 50 to 130 $N*mm^2$.

The nasal implants described herein may be provided in multiple shapes or may be shapeable by the physician to accommodate various anatomies or degrees of collapse. Some configurations may be altered to increase mechanical integrity. This may be achieved, for example, by selectively reducing the space between individual members of an implant design, overlapping portions of the implant, or stacking multiple implants to increase thickness in preferential regions. Preferential flexibility may also be achieved by selectively locking portions of the implant to one another to resist bending. In some embodiments, an implant may include multiple layers that, when rotated or repositioned relative to one another, may change the implant's overall rigidity or rigidity in certain areas and certain orientations. The implants described herein may be able to receive various volumes of fluid prior to implantation or in-situ to modify shape and/or mechanical properties. The implants described herein may be modified to receive a fluid that can include a bioactive agent or pharmaceutical compound to achieve a desired tissue response.

In some embodiments, an implant as described herein may be in the form of a net, weave or braid that may freely move a selective distance in the orthogonal direction from its flat state footprint with minimal force and be incapable of deflecting further from this predetermined distance. This implant may include a flexible or rigid frame of various geometries for the net, weave, or braid that may be fixed to surrounding anatomical structures or tissues. The frame may include features that assist in this fixation, such as barbs, suture eyelets or extending members with tissue engaging features. The nasal implant can have an open structure to allow blood flow to adjacent tissue, such as cartilage.

Implant cross-sections may include multiple longitudinal elements with the same or different dimension, for example, the elements closest to the center of the implant footprint can be thicker or wider to provide more rigidity while the outer most elements can be thinner or narrower to allow for more flexibility. This example would provide more rigid mechanics at the area most likely to need support from collapsing while providing a more atraumatic transition to the perimeter tissue structures requiring less support.

Implants may be made of various polymer configurations throughout or selectively within the implant footprint to allow for various mechanical properties and/or promote various physiologic responses and interactions in/with surrounding tissue. The nasal implants can be made out of a variety of different biocompatible materials. In some embodiments, the nasal implant includes a first bioabsorbable material. In some embodiments, the nasal implant consists essentially of a first bioabsorbable material. The nasal implants can be made out of multiple different materials, such as multiple bioabsorbable materials and a combination of bioabsorbable materials and non-bioabsorbable materials. In some embodiments, the nasal implant can include a non-bioabsorbable material alone or in addition to one or more absorbable materials.

In embodiments where the nasal implant is biodegradable, the degradation properties of the implant can be tailored based on the selection of the materials and optional coatings of the nasal implant. In some implementations, the nasal implant includes a first bioabsorbable material with a first degradation profile and a second bioabsorbable material with a second degradation profile. The first degradation profile can be faster to promote a rapid inflammatory response to help form a protective capsule around the implant that could quickly secure the implant into the targeted position within the nasal tissue. The second degradation profile can have a slower degradation profile and can provide more lasting mechanical support. In some embodiments, the second material can be a non-degradable material. The first degradation profile and optional second degradation profile can be about 2-10 weeks at the low end and 3-5 years on the top end. The profile of 2-10 weeks is similar to conventional wound closure and suture, and the profile of 3-5 years is typical of facial cranial plates, suture anchors, cartilage replacement. Alternatively, the implant may be non-biodegradable and thereby permanent.

In some embodiments, the nasal implants described herein can include a hollow portion or one or more internal implant chambers that can receive a fluid. The fluid can be provided to or removed from the hollow portion or the internal implant chambers to change one or more of the shape, profile, and rigidity of the nasal implant. An example of a fluid that can modify the structural properties of the nasal implant is saline or other biocompatible fluid. In some embodiments, the fluid can include a pharmaceutical or bioactive agent that can be provided to the hollow portion or one or more internal implant chambers. The fluid can be provided to the nasal implant prior to implantation or in-situ after the nasal implant has been placed within the nasal tissue. In one example, a delivery tool for the nasal implant can include a reservoir containing the fluid and a fluid pathway between the reservoir and the nasal implant such that the desired amount of fluid can be provided or removed from the nasal implant in-situ. The hollow portion or one or more internal implant chambers can also be designed to receive the fluid in-situ from a source that is separate from the delivery tool. For example, a needle or syringe could be used to provide the fluid to the nasal implant in-situ.

In some embodiments, the implants described herein or features on the implants may include shape memory material. In some variations, an implant includes a biocompatible, bioabsorbable material such as a bioabsorbable polymer. A bioabsorbable or biodegradable implant may provide structure and support to a body tissue, such as nasal tissue. Part or all of an implant may be degradable in vivo (also referred to as biodegradable) into small parts and may be bioabsorbable. A method as described herein may include biodegrading and bioabsorbing an implant or just part of an implant if an implant includes both bioabsorbable and non-bioabsorbable parts. Bioabsorbing may be facilitated by tissues and organs. Tissues and organs that bioabsorb may include bodily fluids, such as blood, lymph, mucus, saliva, etc. Bacteria may also aid in bioabsorbing a material. An implant may be partially or wholly made from one or more biocompatible biodegradable material, such as from a naturally occurring or synthetic polymer. A biodegradable implant may be made from a poly(lactide); a poly(glycolide); a poly(lactide-co-glycolide); a poly(lactic acid); a poly(glycolic acid); a poly(lactic acid-co-glycolic acid); poly(lactide)/poly(ethylene glycol) copolymers; a poly(glycolide)/poly(ethylene glycol) copolymers; a poly(lactide-co-glycolide)/poly(ethylene glycol) copolymers; a poly(lactic acid)/poly(ethylene glycol) copolymers; a poly(glycolic acid)/poly(ethylene glycol) copolymers; a poly(lactic acid-co-glycolic acid)/poly(ethylene glycol) copolymers; a poly (caprolactone); poly(caprolactone)/poly(ethylene glycol) copolymers a poly(orthoester); a poly(phosphazene); a poly (hydroxybutyrate) or a copolymer including a poly(hydroxybutyrate); a poly(lactide-co-caprolactone); a polycarbonate; a polyesteramide; a polyanhidride; a poly (dioxanone)(PDO); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene) copolymer, or a blend or copolymer thereof. In some examples, an implant includes poly-L-lactic acid (PLLA) or poly-D-lactic acid (PDLA) or both. In some examples, an implant is 90:10, 80:20, 70:30, 60:40, 50:50 PLLA/PDLA copolymer or is in between any of these values. In some examples, an implant is 70:30, +/−10% PLLA/PDLA copolymer. In some examples, an implant is 70:30, +/−10% PLLA/PDLLA.

An implant as described herein may include additional bioactive agents or materials, such as an antibiotic, another antibacterial agent, an antifungal agent, an antihistamine, an anti-inflammatory agent, a cartilage growth inducer, a decongestant, a drug, a growth factor, microparticles, a mucolytic, a radiopaque material, a steroid, or a vitamin. Such materials may be attached to, adhered to, coated onto, or incorporated into an implant. Such materials may be inserted into a body tissue along with the implant. Such materials may be injected into the implant. The materials can be provided to a bladder or a hollow portion of the nasal implant that is configured to receive the fluid from the external source like a syringe or needle. The implant hollow portion or bladder can be configured such that it weeps the active agent at a predetermined rate to the surrounding tissue. The implant could be configured to include multiple hollow portions that can each include an opening or structure on the external surface of the implant that can receive the injections of the active agent in-situ for the designed life of the nasal implant without significant structural compromise. Such materials may be required at different times and may be time sensitive or time release. For example, an anti-inflammatory agent may be useful immediately after implantation to prevent too much early inflammation and pain, but may not be desirable during later stages of scar formation and healing as it may interfere with a healing process that provides new tissue to provide support for tissues. For example, an implant may be configured to release a cartilage growth inducer, such as a fibroblast growth factor (FGF; such as basic fibroblast growth factor or FGF2) or a transforming growth factor (TGF; such as TGFβ1) after several days or weeks so as to prevent an inappropriate or unwanted response early on. Alternatively, the implant may include an active agent or material intended to promote inflammation in the early stages of delivery to promote scar formation that will provide desirable permanent alterations to the surrounding tissue and lateral wall structure. This may be accomplished by incorporating rapidly resorbable materials selectively in direct contact with surrounding tissues in the early stages of implantation to promote a more aggressive foreign body response for an initial predetermined time period approximately 2-12 weeks.

The implants disclosed herein can include multiple materials to tailor the stiffness of the implant, outer hardness/softness, biocompatibility, and absorption profile of the implant. In some embodiments, the implants can include an inner structure that is degradable with an outer coating that is hydrophobic. The degradable material can degrade in vivo through hydrolysis. Degradation can be slowed by coating the degradable material with a coating, such as a hydrophobic coating to control or tune the degradation of the implant. The hydrophobic coating can delay ingress of water and subsequently delay hydrolysis of the degradable portion of the implant. An example of a hydrophobic material that can be used is polycaprolactone, which is an absorbable material that is hydrophobic, crystalline, and highly elastic making it well suited for a coating. The coating can be applied with a specifically selected blend of solvents to minimize the impact on the underlying polymer structure. In some embodiments, a non-absorbable biocompatible coating, such as a silicone, an epoxy acrylate, or Parylene™ can be used to slow the absorption of water into the underlying polymer.

In some embodiments, the biodegradation rate, profile, and/or period of the implant can be tuned. For example, a multitude of coatings both absorbable and non-absorbable can be applied to an underlying implant structure that already exhibits the necessary mechanical properties for supporting upper and lower lateral nasal cartilage. Many possible coatings exist including poly-caprolactone, silicone, fluoropolymers, vinyl alcohol, acrylates, etc. In some embodiments the coating can be Parylene™. An exemplary hydrophobic coating compound, Parylene™ (poly(dichloro-para-xylylene)) has the forms:

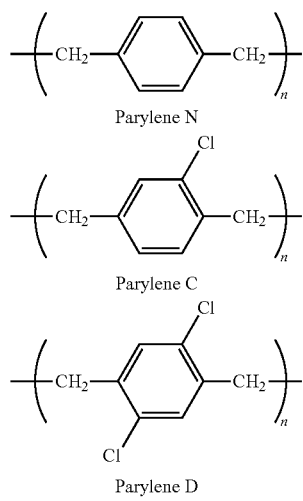

Parylene™ N is the basic member of the family and is typically most permeable to moisture. Parylene™ C and D are typically used for moisture barrier properties. Existing forms of Parylene™ have been primarily used as a complete moisture barrier for electronics and medical implants due to typically pinhole free coating properties. In some cases, Parylene™ can be used as a control release agent for drugs being released out of a material below the coating. For example, the drug can be in a layer or material beneath the Parylene™ coating. In other forms of coatings, Parylene™ can also be used for adding lubricious coatings on guidewires and catheters. In the present disclosure Parylene™ is used differently than the traditional applications. In one embodiment, the semi-permeable nature of extremely thin coating layers can be used advantageously to control water ingress through the thin coating and into contact with the underlying implant structure. The biodegradation rate of the implant can be controlled by selecting and controlling the thicknesses and conformity of the coating, such as a Parylene™ coating. The conformal coating process for Parylene™ is well established and allows for controlling the thickness of the coat on the implant substrate. In order to facilitate some water transmission through the Parylene™ coating and initiate hydrolytic degradation, the implant may be coated at thicknesses in the range of about 0.1 to about 10 microns, preferably in the range of 0.1 to 5 micron to allow for a semi-permeable design. The design of a semi-permeable coat can achieve selective tuning of the absorption rate of the implant, where the extent of permeation is determined by the coating thickness and conformity.

In nasal implant embodiments where a hydrophobic coating is used, the thickness of the hydrophobic coating can be selected to modify the absorption profile of the implant. In some embodiments, the thickness of the hydrophobic coating can be from about 0.1 micron to about 10 microns. In some embodiments, the thickness of the hydrophobic coating can be from about 0.1 micron to about 5 microns. In some embodiments, the thickness of the hydrophobic coating can be from about 0.1 micron to about 1 micron. In some embodiments, the hydrophobic coating has a thickness of less than 10 microns. In some embodiments, the hydrophobic coating has a thickness of less than 5 microns. In some embodiments, the hydrophobic coating has a thickness of less than 1 micron. The thickness of the coating can be selected to control the rate of water ingress through the coating and into the core of the implant. The hydrophobic coating can be applied to the entire outer surface of the implant or portions of the outer surface of the implant. In some embodiments, the hydrophobic coating is applied to a central rod portion of the implant. In another embodiment, the hydrophobic coating is applied to the implant except for the ends. For example, the proximal end or tip can be uncoated to act as a site for water ingress. The conformity of the hydrophobic coating can also be selected to modify the absorption profile of the implant. In some embodiments, the conformity of the hydrophobic coating is selected to control the rate of water ingress through the hydrophobic coating and into the core of the implant. In some embodiments, the hydrophobic coating has a patterned conformity with coated sections and open sections. The patterned hydrophobic coating can be applied over the entire outer surface of the implant or on portions of the implant. In some embodiments, the hydrophobic coating can have a porous structure. In some embodiments, the hydrophobic coating can have a laminated structure made out of multiple materials. For example, a combination of bioabsorbable layers and non-bioabsorbable layers can be used in some embodiments to tune the degradation rate or profile of the implant after implantation in the nasal tissue.

When a coating is used on the nasal implants described herein, the coatings can be applied using a variety of processes, such as vapor deposition, dip coating, spray coating, sputter coating, brush layering, etc. In some embodiments, the coating is bioabsorbable. In the case of polycaprolactone, the coating itself is hydrophobic and bioabsorbable allowing for complete resorption over time. Using a dip coating method, a coating thickness of 0.1 to 10 microns can be achieved for desired results. Additionally, the same effect can be achieved by depositing 0.001 to 20 weight percent of polycaprolactone on the implant substrate. Polycaprolactone is dissolved readily in a mixture of various solvents consisting of but not limited to cycloalkanes, organic esters, chloroform and other such organic solvents.

The degradation profile rate of an implant and/or portion of an implant described herein can be selectively tuned such that the life of the implant core or implant base polymeric substrate can be increased up to 20-fold. The desired biodegradation profile can include a time period of less than about 48 months. The desired biodegradation profile can include a time period of less than about 36 months. The desired biodegradation profile can include a time period of less than about 24 months. The desired biodegradation profile can include a time period of less than about 18 months. The desired biodegradation profile can include a time period of less than about 12 months. The desired biodegradation profile can include a time period of less than about 9 months. The desired biodegradation profile can include a time period of less than about 6 months. The desired biodegradation profile can include a time period of less than about 3 months. The desired biodegradation profile can include a time period of less than about 1 month. The degradation profile can include a time period of 12-18 months.

Delivery methods and tools are also described herein for use with the nasal implants described herein. In some cases, the implants described herein can be delivered using a custom delivery tool. For example, the custom delivery tool can include a handle portion with a hand grippable surface and an elongate member having a proximal end and a distal end with the proximal end engaged with the handle portion. The distal end can include an implant chamber adapted to hold any of the nasal implants described herein and an opening adapted to eject the nasal implant from the implant chamber. The opening can be at the distal end of the elongate member and includes a central axis of the elongate member. The opening can be adjacent to the distal end of the elongate member and orthogonal to a central axis of the elongate member. The delivery tool can further include a cutting surface on the distal end of the elongate member. The cutting surface can be at a distal most end of the elongate member. The cutting surface can include a scissor element with blades at the lateral edges of the scissors such that the lateral edges are adapted to make a planar opening in the nasal tissue when the lateral edges move away from a central axis of the elongate member. The cutting surfaces can be used to separate nasal tissues to form or enlarge the pocket along a plane for placing the implant. For example, the delivery tool can have cutting surfaces similar to tenotomy scissors that have sharp lateral edges that can open to separate and cut tissue in a desired plane.

In some embodiments, a delivery tool for a nasal implant as described herein can include an energy source, an energized surface of the tool adapted to receive energy from the energy source, and a controller adapted to control energy between the energy source and the energized surface of the tool. Examples of the energy source include one or more of cryogenic, ultrasound, and radiofrequency (RF). In one aspect, the energy source can be used to interact with the nasal tissue. The energized surface can be adapted to provide energy to a portion of the nasal tissue to promote a physiological response. In another aspect, the energy source can be used to interact with the nasal implant to activate or change the shape and properties of the nasal implants. The energized surface can be adapted to provide energy to a portion of the nasal implant to change a shape of the nasal implant.

In some embodiments, a delivery tool for a nasal implant as described herein can include a distal portion having an element that is in fluid communication with the implant and proximal handle. This fluid communicating element can be employed to selectively expand or reduce the size of the implant with either injection or removal of fluids from internal implant chambers described herein. For example, the delivery tool can include a fluid source, a fluid injection port adapted to provide fluid into a portion of the nasal implant, and a fluid communication pathway between the fluid source and the fluid injection port. The delivery tool can further include a fluid controller configured to control a flow of fluid between the fluid source and the nasal implant to change a shape of at least a portion of the nasal implant.

A delivery device as described herein can also include controls on the proximal handle to accomplish any of the tasks described herein. For example, the controls can include one or more of triggers, sliders, or rollers to advance a plunging element to push the implant from the distal portion into the target tissue region. The delivery tool may be a single tool or a set of tools.

In some embodiments, a delivery tool as described herein can include a structure for expanding the internal pocket such as a balloon to apply pressure between tissue layers and delaminate or dissect the layers from one another. If a balloon-like expansion is used at the distal region to create a pocket, then the proximal handle can also include a connection to a pressure source or a piston like mechanism to create pressure using a fluid, like a liquid, air, or other gas. A lumen can connect the pressure-creating source at the proximal handle to the balloon at the distal end. The balloon-like expansion may also be created using a braid or coil like structure that can expand to a larger diameter when reduced in length. This may be accomplished by using a structure, such as telescoping rods, at the distal end of the tool that are selectively connected to the distal and proximal ends of the braid or coil member and capable of moving relative to one another to expand or collapse the braid or coil. Another example of a structure that can be used to modify the nasal tissue to separate tissue includes a semi-rigid loop material that can be deployed from an opening in the distal end of the delivery tool. For example, a wire or other similar material can be advanced out of the distal opening in the delivery tool such that a loop is formed that can be expanded such that it dissects and separate nasal tissue along a flat plane corresponding to the loop.

Methods for delivering the nasal implant are also described herein. Methods for placing the implants described herein can be minimally invasive in some cases. In other embodiments, the methods for delivering the nasal implants can be more invasive than a minimally invasive procedure but less invasive than an open surgical techniques. Thus, in some implementations, the methods can be between minimally invasive and open surgical techniques.

In some embodiments, a method of delivery a nasal implant can include creating a pocket within a nasal tissue of a patient and placing any of the nasal implants described herein within the pocket. The pocket within the nasal tissue of the patient can be between the mucosa and the dermis. The pocket within the nasal tissue of the patient can be between the septum and the lateral cartilage. The pocket within the nasal tissue of the patient can be between a mucosa and a nasal septum. The pocket within the nasal tissue of the patient can be between a dermis and a lateral cartilage. The methods can include carrying any of the nasal implants described herein with any of the delivery tools described herein followed by placing the nasal implant by passing the nasal implant through the opening in the elongate member of the delivery tool. The nasal implants can be carried by holding the nasal implant in a compressed state, such as with a compressed length and/or width. The methods can further include suturing the nasal tissue after placing the nasal implant.

In some embodiments, a method of delivery an implant includes delivering the implant in a collapsed state through a small incision and expand in-situ to fill a larger pocket or tissue dissection plane. The nasal implants can be self-expanding or require a method for more active or manual expansion. The expanding nasal implants can include shapes such as spirals, selectively bridged concentric circles, overlapping filament nests, fanned loops, flat stent patterns, shutters, bladder, balloon, etc. The expandable nasal implants can include any of the mechanical or specific geometry designs discussed above to provide selective flexibility when in the expanded state. The expansion capability of these implants from a compressed state can be primarily the result of the flexibility of the polymers used to manufacture the implant in combination with the geometry of the implant. For example, implant configurations that include spaced filament type designs may simply require a reduction in the spacing between filaments and some flex in these filaments to achieve a collapsed state. Other designs, such as substantially round implants may require an ability to flex to a more elliptical shape to reduce dimensions in a preferred direction.

In some embodiments, the methods can include changing a shape of the nasal implant prior to placing the nasal implant within the pocket. In one aspect, applying energy is used to change the shape of the nasal implant. Examples of applying energy include applying one or more of cryogenic, ultrasound, and radiofrequency (RF) to the nasal implant. Thus, in some embodiments, the methods can include applying energy to a portion of the nasal tissue adjacent to the pocket. Additionally, in some embodiments, the methods can include injecting a fluid into a portion of the nasal implant to change a shape of at least a portion of the nasal implant. In one aspect, injecting fluid is done prior to placing the nasal implant within the pocket. In one aspect, injecting fluid is done in-situ.

Thus, described herein are implants that, when delivered, provide broad support of the nasal lateral wall. The implants described herein can be substantially flat. For example, the implants can be 3-5 mm wide, 3 mm or more in height, and 1 mm or less in thickness. The implants can be preferentially flexible to accommodate natural nasal contours while being rigid enough as a whole to prevent internal medial collapse of the nasal wall upon inhalation. Additionally, in at least some embodiments, the nasal implants described herein can be compressible and expandable (e.g., via elastic expansion) for delivery.

Figure 43A:
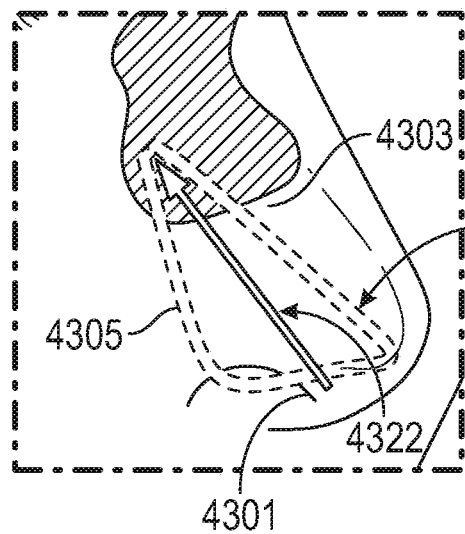
FIGS. 43A-43C show relative positioning of nasal implants as described herein within the nasal anatomy.
Figure 43B:
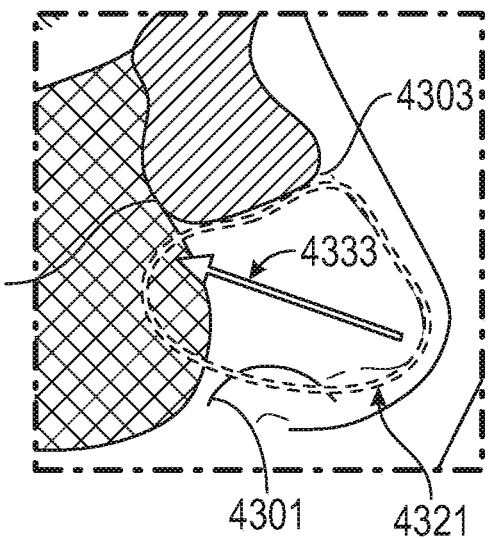
Figure 43C:
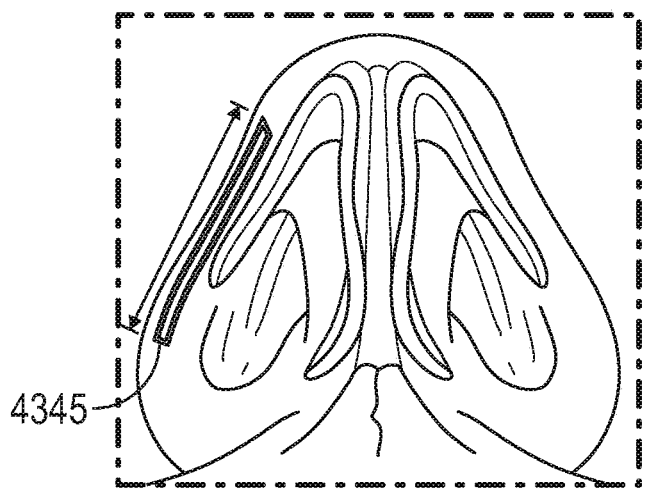

In general, the implants described herein can be placed within the nasal anatomy as shown in FIGS. 43A-43C. That is, as shown in FIG. 43A, an implant can lie along the trajectory of arrow 4322 while spanning the region 4323 (e.g., the region between the nasal dorsum 4303, the maxilla/nasal bone 4305, and the alar rim 4301 of the nasal anatomy). As shown in FIG. 43B, in some embodiments, the implant can have a transverse trajectory along the arrow 4333 such that it cantilevers off of the maxilla/nasal bone 4305, but still sits between the nasal dorsum 4303 and the alar rim 4301. A view of an implant location 4345 from the bottom of the nasal anatomy is shown in FIG. 43C. As shown, the nasal implant can fit between the mucosa and dermis of the nasal lateral wall, such as between the mucosa and the nasal septum.

Figure 3A:
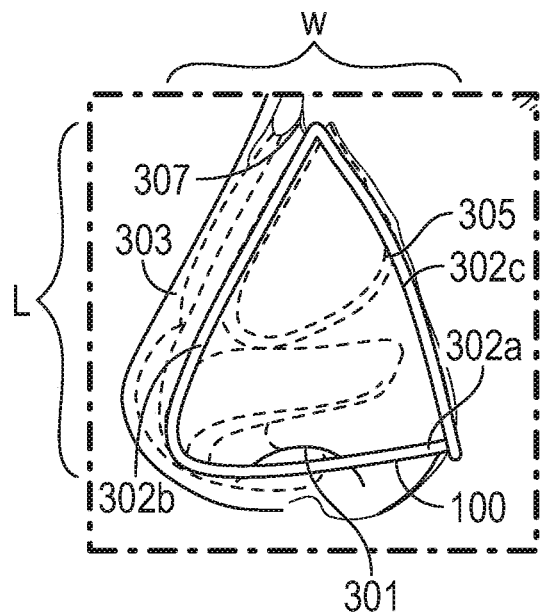
FIGS. 3A-3D illustrate exemplary nasal implants having a substantially triangular profile.
Figure 3B:
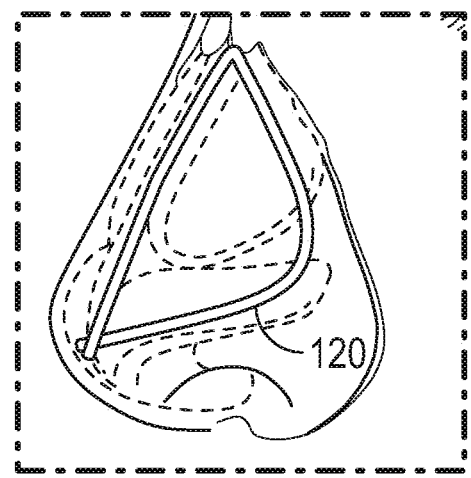
Figure 3C:
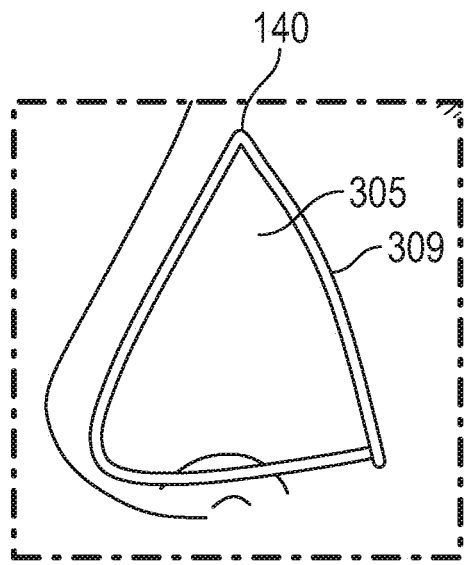
Figure 3D:
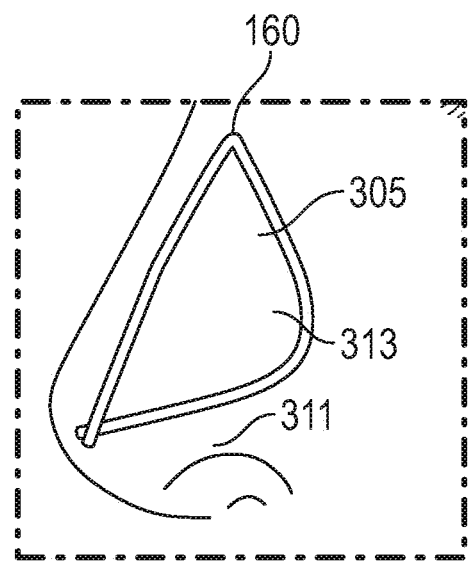

Exemplary implants 100, 120, 140, 160 are shown in FIGS. 3A-3D in various positions within the anatomy. FIG. 3A illustrates a nasal implant 100 with a triangular outer profile within the nasal anatomy. The implant 100 is thus comprised of three separate struts 302a,b,c. The implant 100 is configured to sit such that the outer profile (e.g., formed by the struts 302a,b,c) borders the nasal dorsum 303, the maxilla/nasal bone 305, and the alar rim 301 of the nasal anatomy. The nasal implant has a width W that extends along the alar rum 301 and a length L that extends from the alar rim up to the top of the upper lateral cartilage 307. The width W can be less than then length L. The triangular configuration of the nasal implant 100 can advantageously provide support to the nasal anatomy. In some embodiments, two or more of the sides of the implant 100 can be compressible relative to one another during delivery to allow the implant 100 to compress to a smaller size. FIG. 3B illustrates another exemplary nasal implant 120 with a triangular profile and positioned within the anatomy in a similar manner as in FIG. 3A. The nasal implant 120 is similar to implant 100 except that the implant 120 has a shorter length than the nasal implant 100. FIG. 3C illustrates another exemplary nasal implant 140 with a triangular profile. The implant 140 includes a portion 309 that is configured to extend over the nasal/maxilla bone 305 to form a foundational anchor point (i.e., the portion 309 can support the rest of the implant 140 as a cantilever). FIG. 3D illustrates a nasal implant 160 spanning from the septum 311 to the nasal/maxilla bone 305 at the lateral aspect of the piriform aperture 313. The positioning of the implant 160 shown in FIG. 3D allows the implant 160 to act more as a beam supported at either end than like the cantilever support provided by nasal implant 140 as oriented in FIG. 3C.

Figure 4:
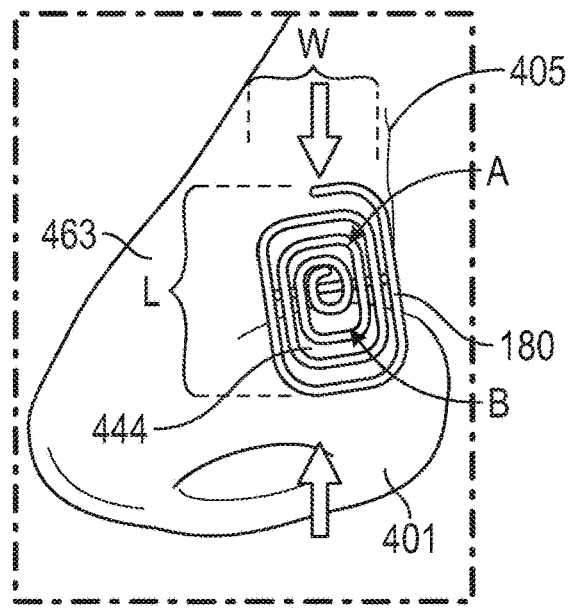
FIG. 4 illustrates an exemplary coiled nasal implant.

FIG. 4 illustrates another exemplary nasal implant 180. The implant 180 has a rounded rectangular or substantially circular profile formed by a spiraled wire (which can be made of metal, polymer, or any other material described herein). The spiral configuration of implant 180 is formed by four loops of the wire. Further, the spiraled configuration can include spaces 444 between two or more adjacent loops of the wire. Like implant 100, the implant 180 can have a length L and a width W that allows it to fit substantially within the boundaries of the nasal dorsum 403, the maxilla/nasal bone 405, and the alar rim 401. The wide area of the implant 180 (e.g., the area in the plane of the spiraled profile) can ensure that little deformation or collapse of the nasal anatomy can occur as a force is applied across the profile (e.g., into the page in FIG. 4), as might occur during inhalation. At the same time, however, the spiraled configuration can provide for flexibility of the implant along the profile at discrete locations to substantially conform to the contours of the nasal anatomy during implantation. For example, the implant 180 might flex or bend in a direction perpendicular to the spiraled profile (e.g., into the page in FIG. 4) at location A and also bend or flex in a direction perpendicular to the spiraled profile (e.g., out of the page in FIG. 4) at location B while adjacent or neighboring loops remain unflexed. Further, the spaces 444 between adjacent loops can advantageously allow the loops of the implant 180 to move closer together (e.g., if compressed in the direction of the arrows). Such compression can be useful, for example, during delivery of the implant 180. Because of its broad coverage, the nasal implant 180 can provide robust mechanical support to the nasal tissue extending from the nasal dorsum 403 to the maxilla/nasal bone 405 to the alar rim 401.

Figure 5A:
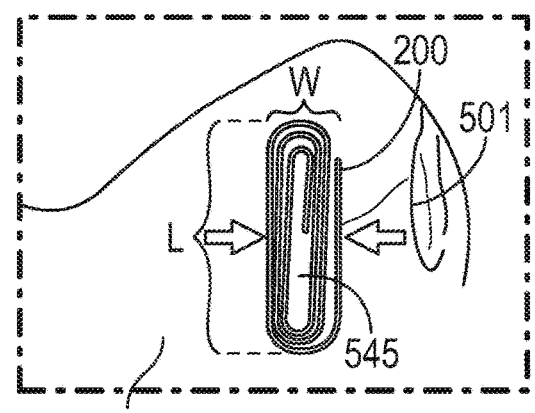
FIGS. 5A-5B illustrate exemplary looped nasal implants.
Figure 5B:
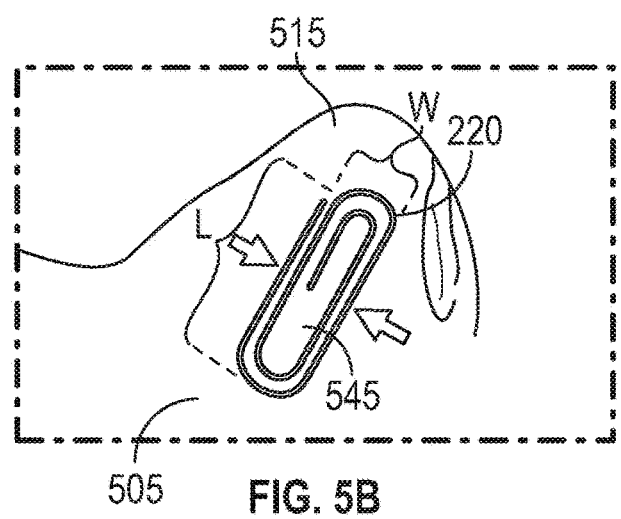

FIGS. 5A-5B illustrate additional exemplary nasal implants 200, 220. The nasal implants 200, 220 are similar to nasal implant 180 except that they have a longer length L and a shorter length W to form a substantially oval profile. Additionally, the implants 200, 220 have larger space 545 in the center of the spiral than the space in the center of the spiral of implant 180. Implant 200 has between 3-4 loops of wire while implant 220 has between 2 and 3 loops of wire. The nasal implants 200, 220 are illustrated with slightly different positions relative to the nasal anatomy. The length L of the implant 200 extends substantially parallel with the alarm rim 501. In contrast, the length L of the implant 220 extends along a line from the maxilla/nasal bone 505 towards the columella 515. Like implant 180, implants 200 and 220 can compress during delivery (e.g., in the direction of the arrows). Additionally, like implant 180, implants 200 and 220 can flex at discrete locations along the loop to conform to the nasal anatomy while providing an overall rigid backstop to collapse of the nasal anatomy, e.g., during inhalation.

Figure 9A:
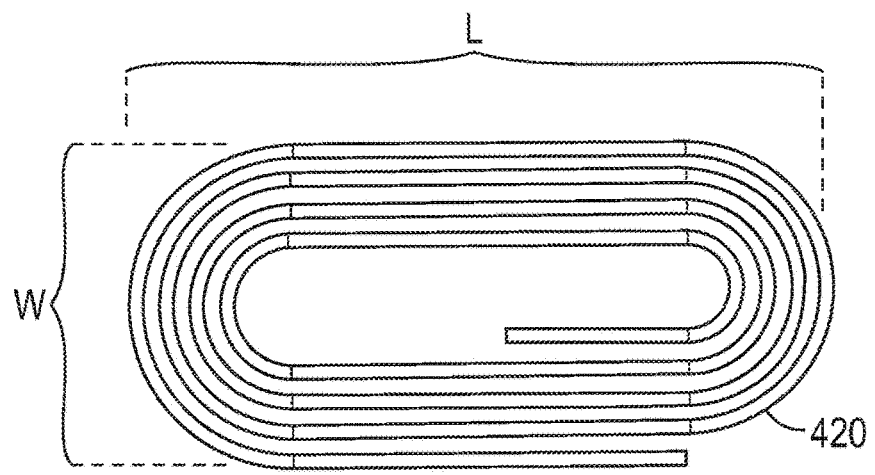
FIGS. 9A-9C illustrate exemplary looped nasal implants.
Figure 9B:
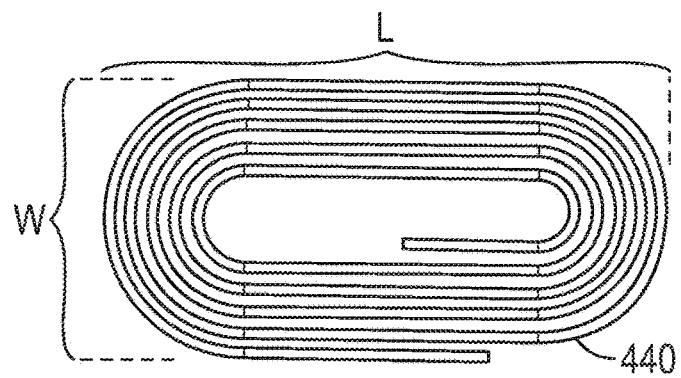
Figure 9C:
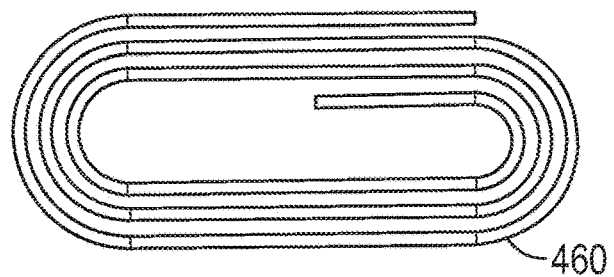

FIGS. 9A-9C show implants 420, 440, 460 that are similar to implants 200, 220 of FIG. 5A-5B. The nasal implant 420 has an oval type profile formed by a spiraled wire. The spiral configuration of nasal implant 420 is formed by approximately four loops of the wire. FIG. 9B illustrates a nasal implant 440 having an oval type profiled formed by five loops of spiraled wire. FIG. 9C illustrates a nasal implant 460 having an oval type profile formed by three loops of spiraled wire. The wire used for nasal implant 460 has a larger diameter than the wire used for nasal implant 440.

Figure 6A:
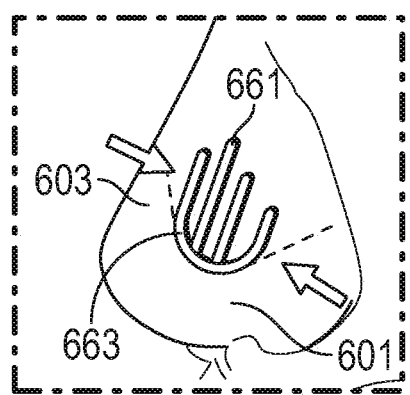
FIGS. 6A-6B illustrate nasal implants including projections.
Figure 6B:
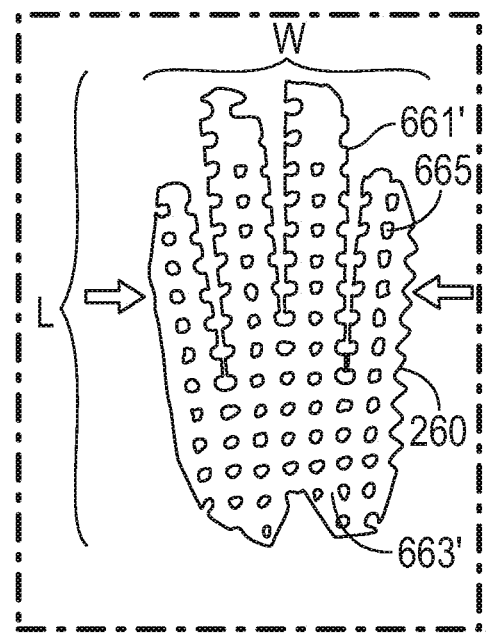
Figure 6C:
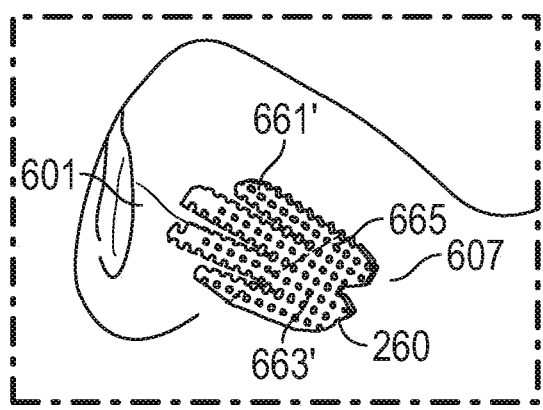
FIGS. 6C-6D illustrate various positions for the nasal implant shown in FIG. 6B.
Figure 6D:
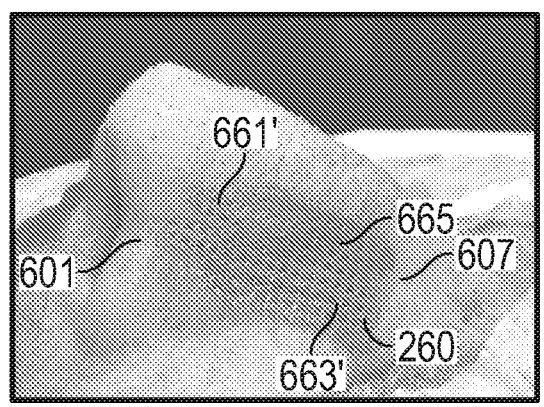

FIGS. 6A-6B illustrate additional exemplary nasal implants 240, 260 that can be flexible at discrete locations, compressible in at least one direction, and provide a rigid backstop to deformation of the nasal anatomy. The nasal implant 240 shown in FIG. 6A has a plurality of finger-like projections 661 extending from a base 663 of the implant 240. As shown in FIG. 6A, the implant 240 can be positioned such that the base 663 is positioned close to the alarm rim 601 while the projections 661 extend upwards substantially parallel with the nasal dorsum 603. The finger-like projections 661 can advantageously provide flexion or bending of the implant 240 as necessary to conform to the nasal anatomy. However, the overall profile of the implant 240 can be rigid enough to resist a force across substantially the entire profile due, for example, to inhalation. The spacing between the projections 661 can also allow for compression of the implant 240 in the direction of the arrows, e.g., to make the implant 240 more easily delivered. The implant 260 shown in FIGS. 6B-6D is similar to implant 240. However, implant 260 includes a plurality of perforations or openings 665 therethrough, e.g., to provide added flexibility and/or allow fluid flow therethrough. FIGS. 6C and 6D show exemplary positioning of the implant 260 in the nasal anatomy. As shown, the implant 260 can be positioned such that the base 663' is positioned near the top of the upper lateral cartilage 607 while the projections 661' stretch towards the alar rim 601. Further, FIGS. 6C and 6D show how the fingers 661' can conform to the contours of the nasal anatomy (while the overall implant 260 can provide resistance to deformation during inhalation).

Figure 13A:
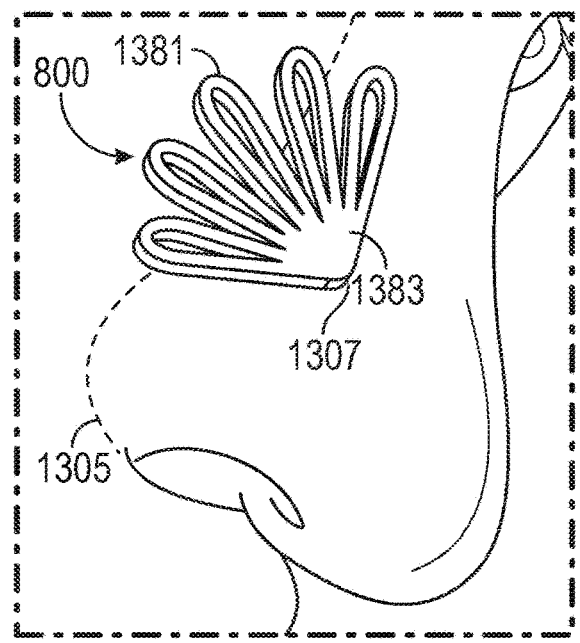
FIGS. 13A-13D illustrate exemplary nasal implants.
Figure 13B:
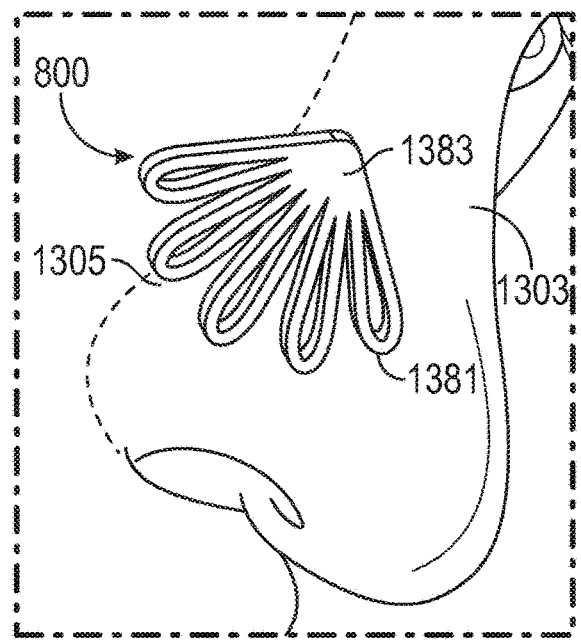
Figure 13C:
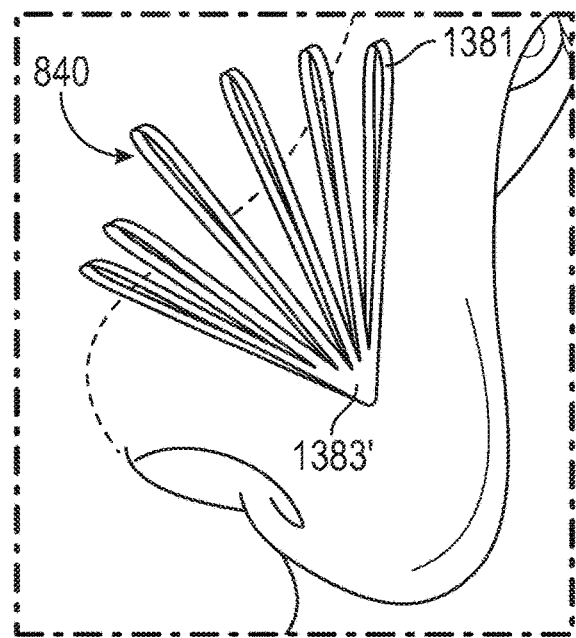
Figure 13D:
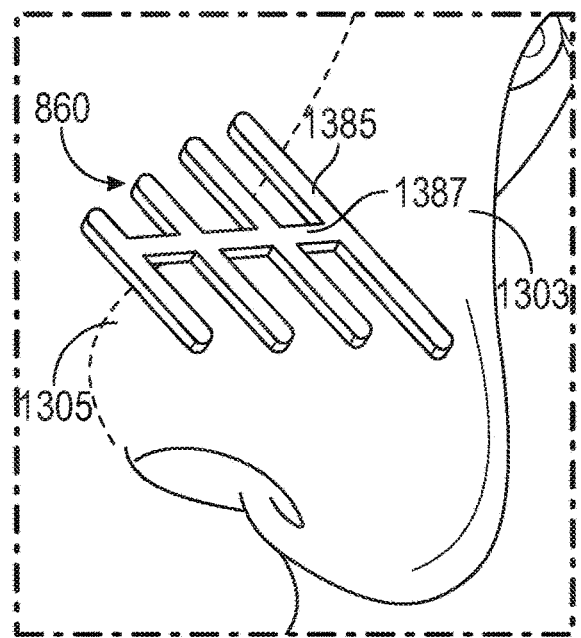

FIGS. 13A-13D show implants 800, 840, 860 that are similar to nasal implants 240, 260 and similarly can be flexible at discrete locations, compressible in at least one direction, and provide a rigid backstop to deformation of the nasal anatomy. That is, FIG. 13A illustrates an implant 800 that includes a base 1383 with a plurality of looped projections 1381 (e.g., five looped projections 1381) extending therefrom where the loops extend within the plane or profile of the implant 800. The implant 800 is shown as being positioned across the maxilla/nasal bone 1305 with the base 1383 positioned along the upper lateral cartilage 1307 and the projections 1381 pointing up towards the eye. The implant 800 can be, for example, placed under the dermis. FIG. 13B shows the same implant 800 implanted in a different position within the nasal anatomy. In FIG. 13B, the base 1383 is positioned closer to the upper portions of nasal dorsum 1303 while the projections 1381 point out towards and/or over the maxilla/nasal bone 1305. FIG. 13C illustrates an implant 840 that is similar to implant 800 and positioned within the nasal anatomy similarly. Unlike implant 800, however, the loops 1381' of implant 840 loop in a plane that is perpendicular to the plane or profile of the implant 800 (the plane that includes the base 1383' and all of the projections 1381'). FIG. 13D shows an implant 860 having a plurality of projections 1385 connected together with struts 1387 in a trapezoidal configuration. The nasal implant 860 is positioned in the nasal anatomy such that the implant extends over the maxilla/nasal bone 1305 while the projections 1385 extend substantially parallel with the 1303 nasal dorsum 1303.

Figure 37:
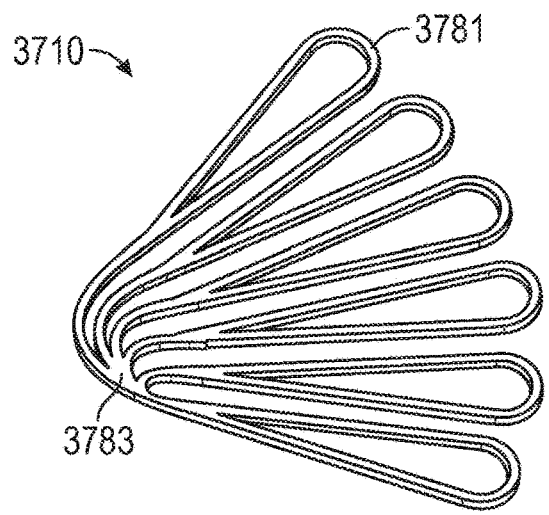
FIG. 37 shows an exemplary nasal implant.

FIG. 37 shows an implant that is similar to implant 800 and includes a base 3783 with looped projections 3781 extending therefrom (six looped projections are shown in FIG. 37). As shown, the projections 3781 can spiral or curve slightly away from the base 3781 in a fan-like configuration.

FIGS. 7A-7F illustrate additional exemplary nasal implants 280, 300, 320, and 340 that can be flexible at discrete locations, compressible in at least one direction, and provide a rigid backstop to deformation of the nasal anatomy. As shown in FIG. 7A, nasal implant 280 has a triangular configuration with a mesh 771 and/or series of wires extending through the center of the triangle. The implant 280 can be compressed (e.g., in the direction of the arrows in 7A) to take on a compressed or compact configuration as shown in FIG. 7B. Like other embodiments descried herein, the mesh and/or wires in the center of the implant 280 can help ensure that the implant 280 is flexible enough to conform to the anatomy yet strong enough to resist collapse, e.g., during inhalation. FIG. 7C illustrates a nasal implant 300 that is similar to implant 280, but has a circular profile. FIG. 7D illustrates a nasal implant 310 that has a circular profile, but does not include the mesh in the center thereof. FIG. 7E shows an implant 320 with a spiral configuration formed by a plurality of undulating wires. FIG. 7F shows an implant 340 in a flower petal type configuration formed by a plurality of wires or weaved wires.

Figure 8L:
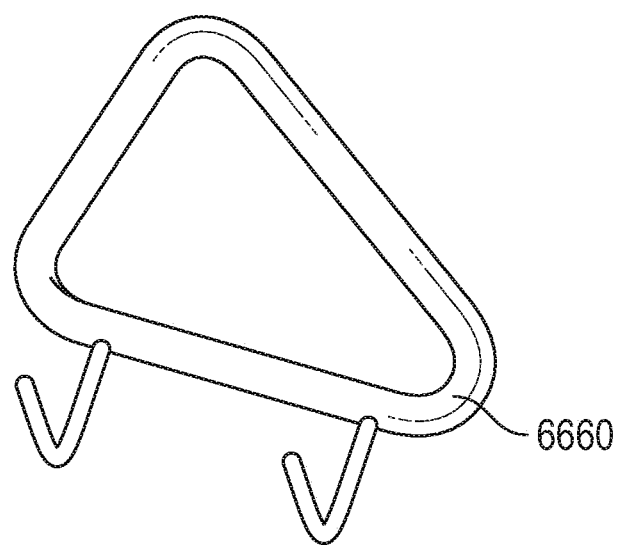
Figure 8M:
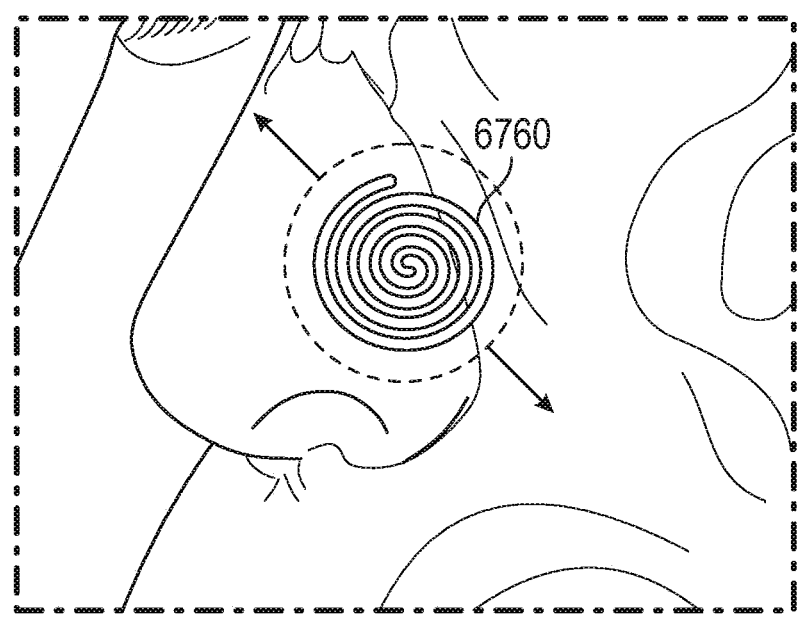

FIGS. 8A-8M illustrate various examples of nasal implants with similar features and/or properties as other implants described herein. FIG. 8A shows an implant 5560 having a spiral oval profile. FIG. 8B shows an implant 5660 having a barbed profile. FIG. 8C shows an implant 5760 with two parallel rods and crisscrossed wires extending therebetween. FIG. 8D shows an implant 5860 having the shape of a rod with a bulbous end. FIG. 8E shows an implant 5960 having two rectangular portions connected together with one or more thin strips. FIG. 8F shows an implant 6060 including a wire in an undulating pattern. FIG. 8G shows an implant 6160 having a spiraled wire in a rounded rectangular profile. FIG. 8H shows an implant 6260 in a circular spiral configuration. FIG. 8I shows an implant 6360 having two parallel rods with wires extending therebetween. FIG. 8J shows an implant 6460 having a solid circular profile with a plurality of perforations extending therethrough. FIG. 8K shows an implant 6560 having a square profile with a row of perforations and a slot extending therethrough. FIG. 8L shows a nasal implant 6660 having a triangular configuration with two barbs extending therefrom. FIG. 8M shows a nasal implant 6760 having a circular spiral configuration.

Figure 17C:
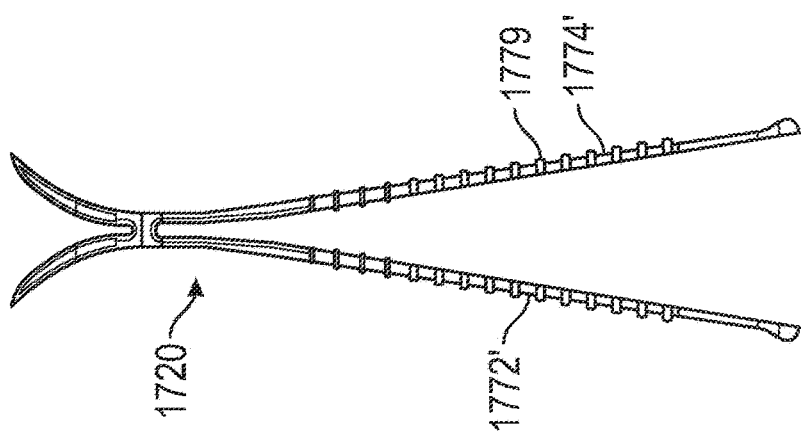
FIGS. 17A-17F illustrate exemplary nasal implants having a pair of elongated members hinged together.
Figure 17B:
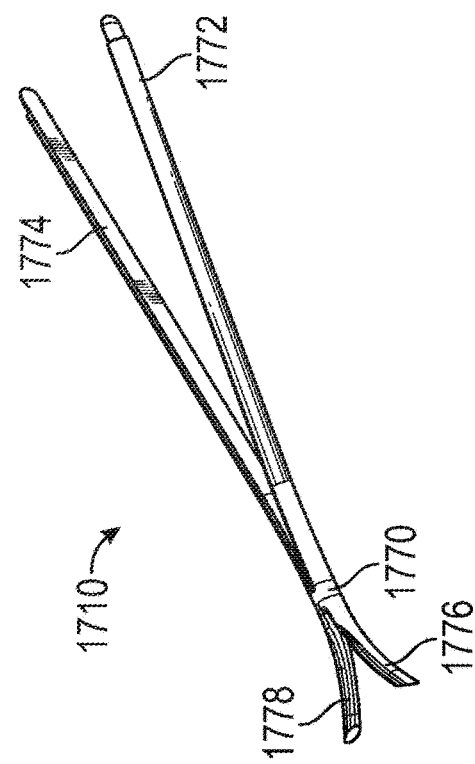
Figure 17A:
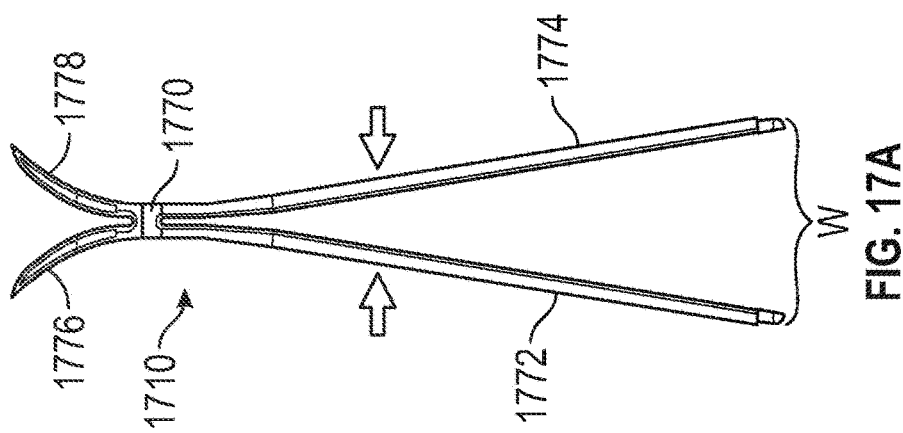

FIGS. 17A-17F show exemplary nasal implants 1710, 1720, 1730 that can be flexible at discrete locations, compressible in at least one direction, and provide a rigid backstop to deformation of the nasal anatomy. As shown in FIGS. 17A-17B, the implant 1710 includes two elongate members 1772, 1774 having blunt atraumatic proximal ends. The elongate members 1772, 1774 are connected together at a junction 1770, which can act as a pivot for the two elongate members 1772, 1774 such that the elongate members 1772, 1774 can move towards one another when compressed as shown by the arrows in FIG. 17A. The elongate members 1772, 1774 can be rounded on the outer edges, but flat on the inner edges thereof so as to provide for greater compactness during delivery. The implant 1710 can further include two barbs 1776, 1778 on the distal ends thereof configured to anchor the implant 1710 into the nasal anatomy. The elongate members 1772, 1774 can have a small enough diameter and/or flexing features therein to allow the implant 1700 to flex at discrete locations as necessary to conform to the local nasal anatomy. Further, the width W of the implants (see FIG. 17A) can be 3-8 mm, such as approximately 5 mm, to provide coverage of a large span of the nasal anatomy. The split structure of the elongate members 1772, 1774 can advantageously provide support to the lateral wall along multiple tracks.

Figure 17D:
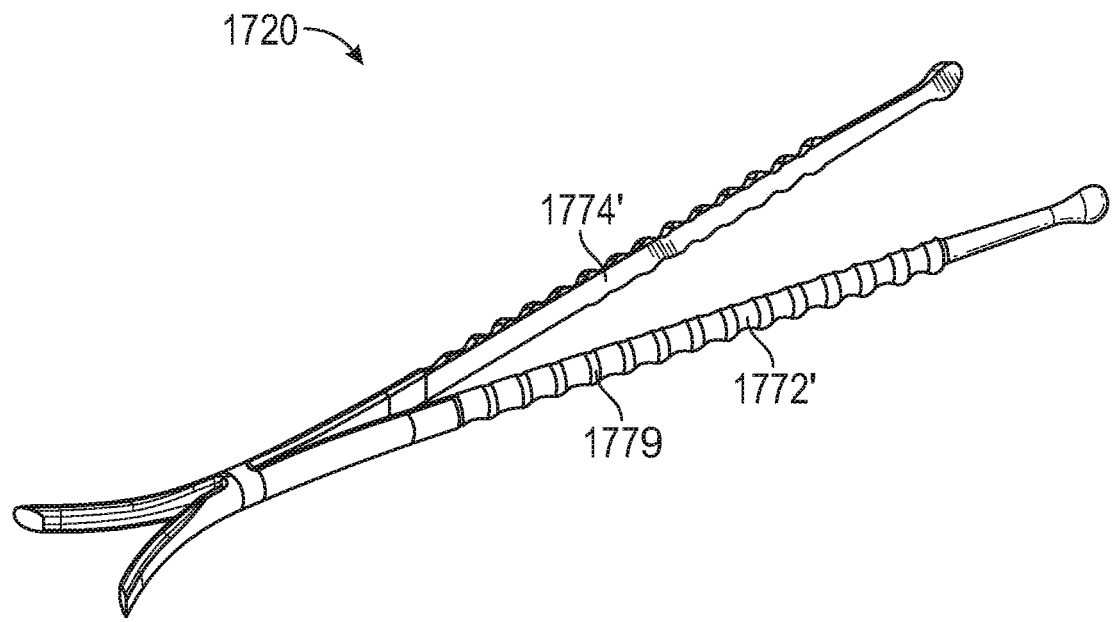
Figure 17E:
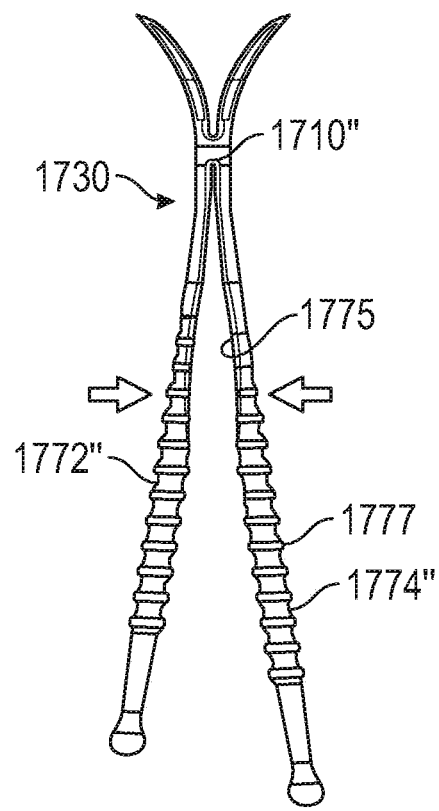
Figure 17F:
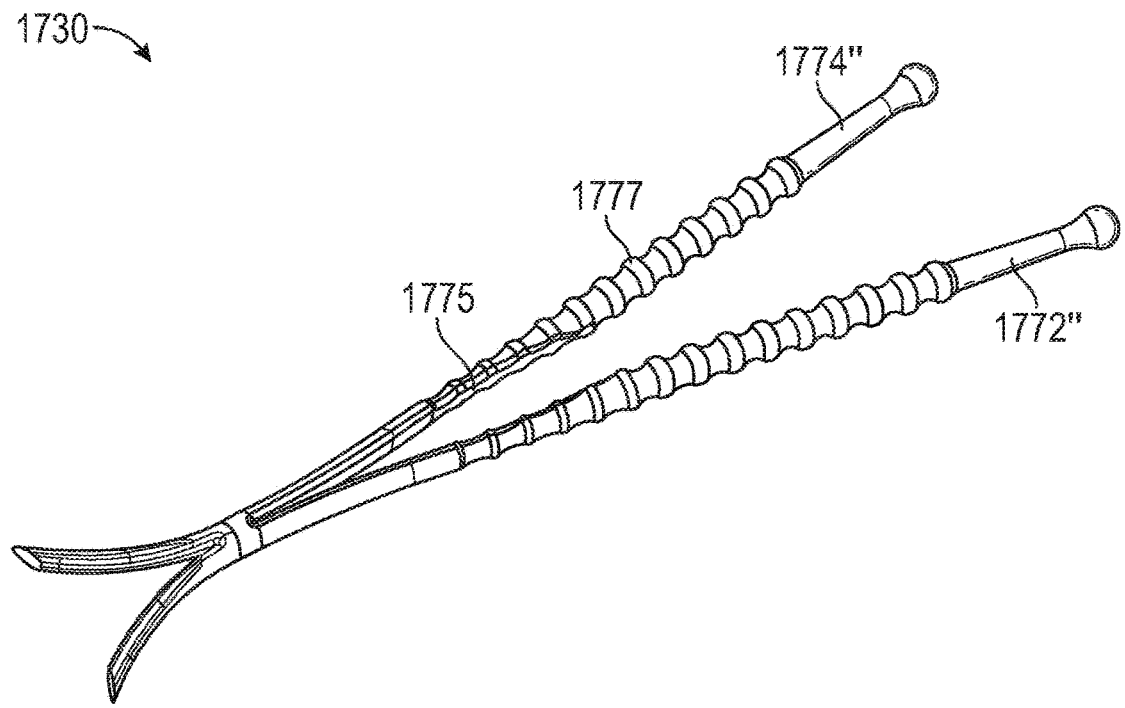

As shown in FIGS. 17C-17D, implant 1720 can be similar to implant 1710 except that the elongate members 1772', 1774' can include bumps 1779 or ridges on the outer edges thereof. As shown in FIG. 17E-17F, implant 1730 can be similar to implant 1720 except that the elongate members 1772" and 1774" include bumps 1777 that extend all the way around the circumference thereof. Additionally, the elongate members 1772", 1774" can be have substantially circular cross sections at the proximal ends but cut-outs 1775 on the inner surface thereof close to the junction 1770" to allow the implant 1730 to be more compact when compressed together in the direction of the arrows. Implant features that can be used, for example, with implants 1710, 1720, 1730 are also described in International Application No. PCT/US17/68419, filed Dec. 26, 2017, title "NASAL IMPLANTS AND METHODS OF USE", the entirety of which is incorporated by reference herein.

Figure 17G:
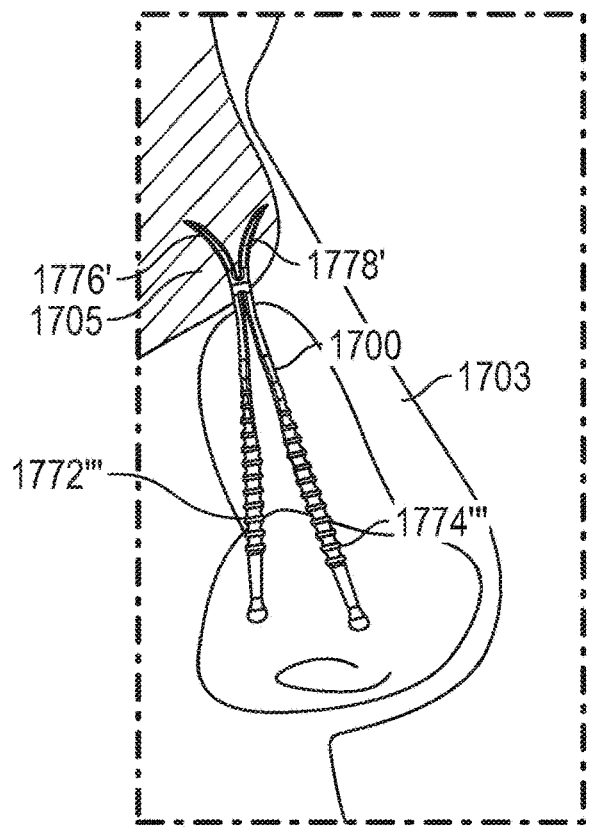
FIG. 17G shows placement of a nasal implant similar to the implants of FIGS. 17A-17F in the nasal anatomy.

Placement of an implant 1700 (which can be similar to any of implants 1710, 1720, 1730) in the nasal anatomy is shown in FIG. 17G. The body of the implant 1700 (including elongate members 1772''', 1774''') can sit between the maxilla/nasal bone 1705 and the nasal dorsum 1703 over the upper and lower nasal cartilage 1788. Barbs 1776' and 1778' can rest over the bone maxilla/nasal bone 1705. The implant 1700 can advantageously be rigid enough that when a force is placed upon the entire implant (e.g., a force into the page in FIG. 17G as would be applied during inhalation), the implant 1700 can resist collapsing of the nasal anatomy.

Figure 33:
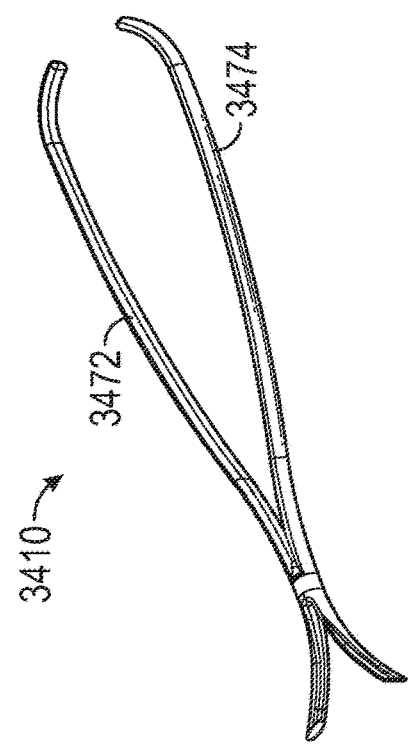
FIG. 33 shows an exemplary nasal implant with a collapsible hinge.

FIG. 33 shows an implant 3310 that is similar to implant 1710 except that implant 3310 includes a collapsible hinge 3333 between the elongate members 3372, 3374. The collapsible hinge 3333 can collapse for delivery (e.g., when pulled proximally), but can hold the elongate members 3372, 3374 apart after delivery to provide support over a larger area of the nasal anatomy. In some embodiments, the collapsible hinge 3333 can be configured to interact with a delivery tool so as to expand and lock after the implant 3310 is in the desired location.

Figure 34A:
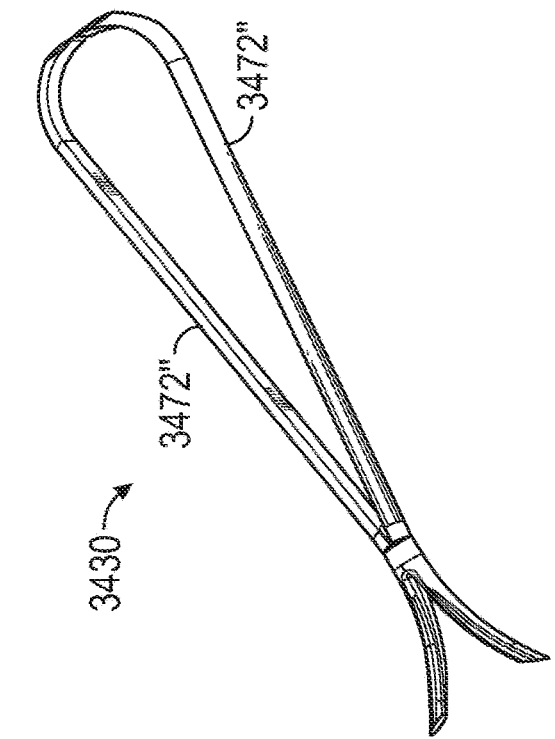
FIG. 34A-34C show exemplary nasal implants.
Figure 34B:
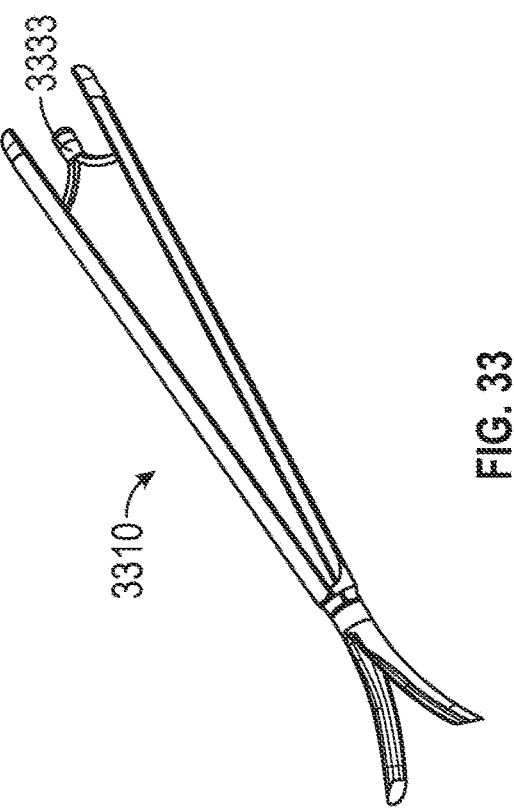
Figure 34C:
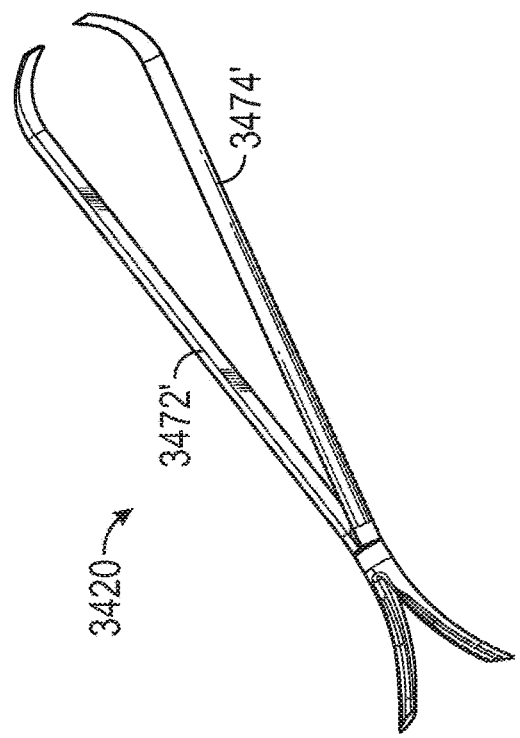

FIGS. 34A-34C show implants 3410, 3420, 3430 that are similar to implant 1710 except that the proximal ends of the elongate members 3472, 3474 are curved inwards towards one another so as to provide an atraumatic end.

FIGS. 19A-19D show additional exemplary nasal implants 1910, 1920, 1930, 1940 that can be flexible at discrete locations, compressible in at least one direction, and provide a rigid backstop to deformation of the nasal anatomy. As shown in FIG. 19A, the implant 1910 includes an arced profile with two wide legs or sections 1991a,b connected by a central junction 1993 (e.g., a curved junction). As shown in FIG. 19A, the wide sections 1991a,b can have atraumatic proximal ends, each with a central tear-drop opening 1995a,b formed therein. The junction 1993 can act as a pivot for the two sections 1991a,b such that the sections 1991a,b can move towards one another (or even over one another) when compressed as shown by the arrows in FIG. 19A. The two wide legs 1991a,b can advantageously flex relative to one another to allow for conformation to the nasal anatomy during implantation. Additionally, the opening 1995a,b can help ensure flexibility of the implant to as to provide conformation to the nasal anatomy. Further, the width W can be between 3-5 mm to provide large coverage of the nasal anatomy.

Figure 19E:
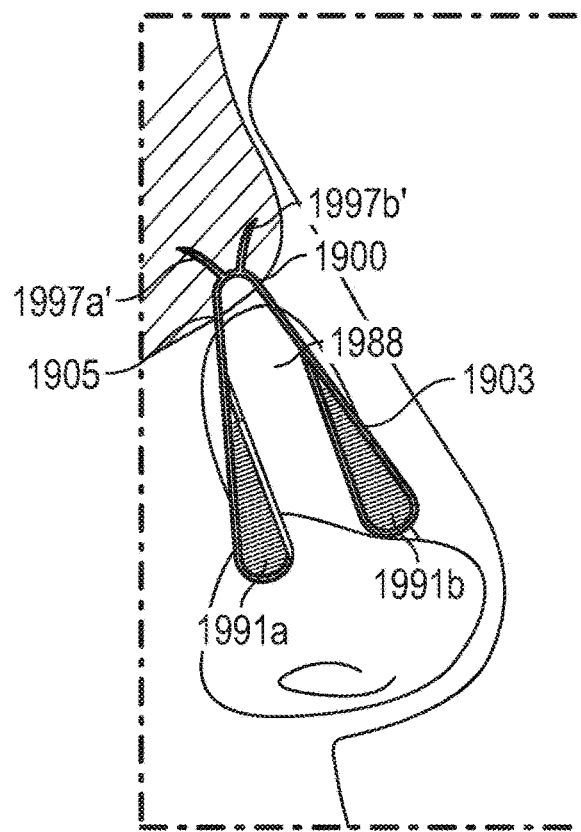
FIG. 19E shows placement of a nasal implant such as that shown in FIGS. 19A-19D in the nasal anatomy.

Implant 1920 shown in FIG. 19B is similar to implant 1910 except that it includes two barbs 1997a,b that can help anchor the implant 1920 in tissue. Implant 1930 shown in FIG. 19C is similar to implant 1920 except that a mesh or perforated material 1999a,b (shaped as a tear-drop) replaces the openings 1995a,b. The mesh or perforated material 1999a,b can advantageously still be flexible enough to provide conformation to the nasal anatomy, but can provide improved rigidity to the overall implant. Implant 1940 shown in FIG. 19D is similar to implant 1910 except that the tear-drop openings 1995a' and 1995b' are longer so as to extend all the way to the junction 1993'. Placement of an implant 1900 (which can be similar to any of implants 1910, 1920, 1930, 1940) in the nasal anatomy is shown in FIG. 19E. The body of the implant 1900 (including legs 1991a' and 1991b') can sit along the maxilla/nasal bone 1905 and the nasal dorsum 1903 over the upper and lower nasal cartilage 1988. Barbs 1997a' and 1997b' can rest over the bone maxilla/nasal bone 1905. The implant 1900 can advantageously be rigid enough that when a force is placed upon the entire implant 1900 (e.g., a force into the page in FIG. 19E as would be applied during inhalation), the implant 1900 can resist collapsing of the nasal anatomy.

FIGS. 31A-31D show exemplary nasal implants 3110, 3120, 3130, 3140 that are similar to the implants of FIGS. 19A-19D. Implant 3110 (shown in FIG. 31A), for example, is similar to implant 1910 except that the loops 3113a,b forming the wide sections 3191a,b are not connected at the distal end (near junction 3193). This can make the implant 3110 more flexible along the profile (e.g., into the page in FIG. 31A) to conform to the nasal anatomy and also make the implant 3110 more easily compressible (e.g., in the direction of the arrows). The implant 3120 (shown in FIG. 31B) is also similar to implant 1910 except that the tear drop openings 3195a and 3195b are smaller (e.g., only half the length of the sections 3191a', 3191b'). The implant 3130 (shown in FIG. 31C) is similar to implant 1940 except that a mesh or perforated material 3199a,b (shaped as a tear-drop) replaces the openings 1995a and 1995b. The implant 3140 (shown in FIG. 31D) is similar to implant 1930 except that there is a solid material 3197 rather than a perforated material.

Figures 20A, 20B:
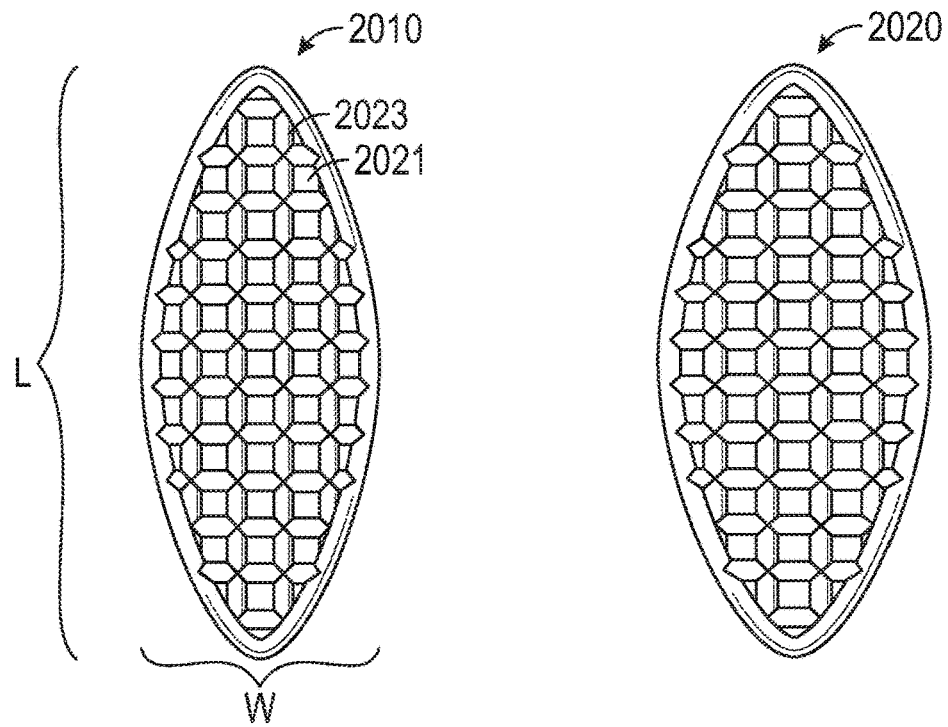
FIGS. 20A-20B show exemplary mesh nasal implants.
Figure 21:
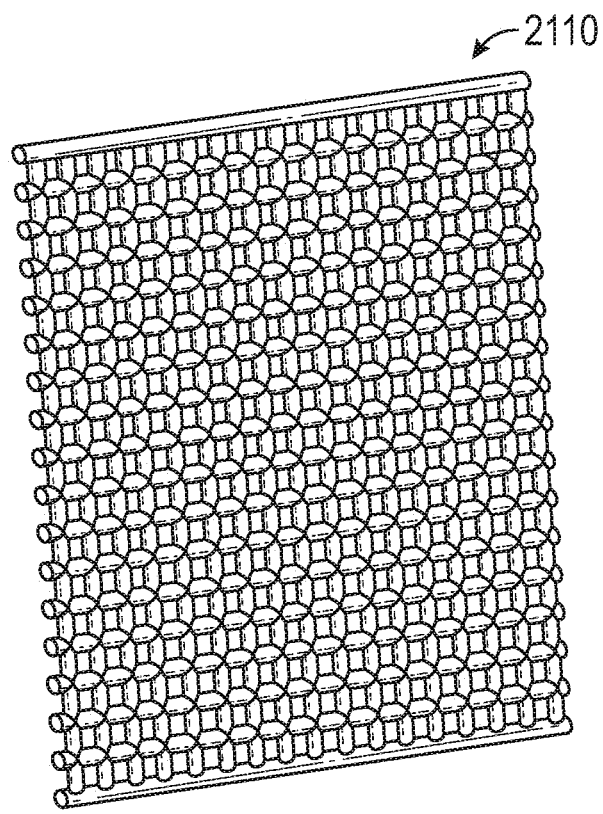
FIG. 21 shows another exemplary mesh implant.

FIGS. 20A-21 show exemplary nasal implants 2010, 2020, 2110 that can be flexible at discrete locations, compressible in at least one direction, and provide a rigid backstop to deformation of the nasal anatomy. Referring to FIGS. 20A-20B, the implant 2010 is in an oval shape and is formed of a plurality of struts 2023 having a series of openings 2021 therebetween (e.g., the implant 2010 can be in the form of a mesh). The openings 2021 can advantageously allow the implant 2010 to compress (e.g., during delivery) as the struts 2023 of the implant 2010 move closer together. Additionally, the openings 2021 can allow the struts 2023 to flex to conform to the nasal anatomy during implantation. The implant 2010 can be, for example, 15-20 mm in length L by 5-7 mm in width W, such as 17 mm in length by 6.25 mm in width. In some embodiments, the implant 2010 can be configured to be trimmed to better fit a specific patient's nasal anatomy. Further, in some embodiments, the implants 2010 can come in varying thicknesses. Other sizes are also possible. For example, implant 2020 shown in FIG. 20B is similar to implant 2010 except that it has a wider width (for example, the width can be 6.5-7.5 mm, such as 7 mm. FIG. 21 shows an exemplary nasal implant 2110 that is similar to implants 2010 and 2020 except that it has a square shape (which can again be trimmed to better conform to the patient's nasal anatomy).

Figure 24:
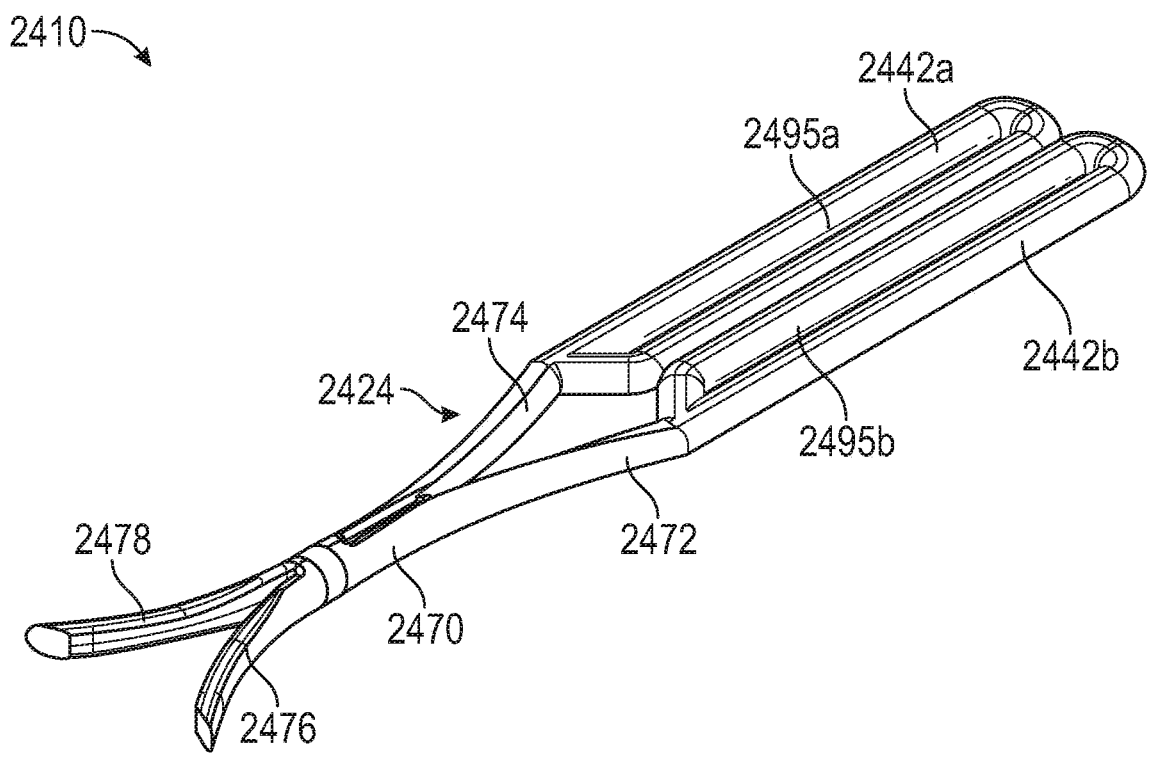
FIG. 24 shows an exemplary nasal implant.
Figure 25:
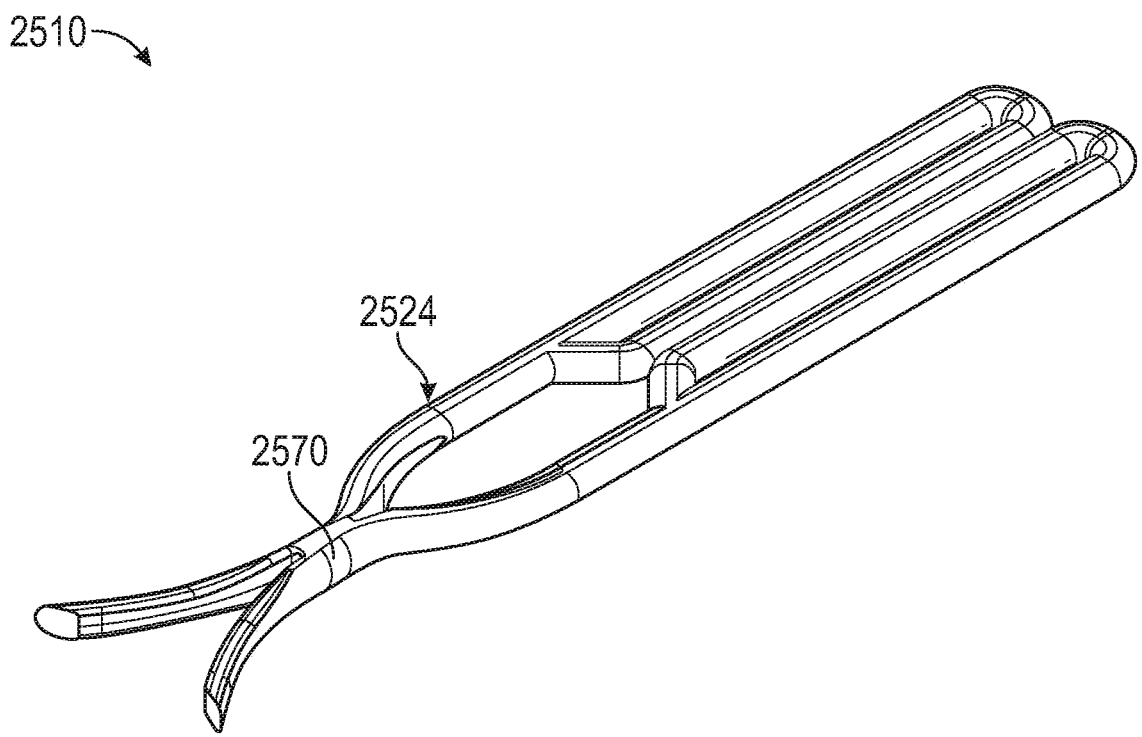
FIG. 25 shows an exemplary nasal implant.

FIGS. 24-25 show implants 2410, 2510 that that can be flexible at discrete locations, compressible in at least one direction, and provide a rigid backstop to deformation of the nasal anatomy. Referring to FIG. 24, the implant 2410 is similar, for example, to implant 1710 in that it includes two elongate members 2472, 2474 that meet at a junction 2470 as well as two barbs 2476, 2478 at the distal end thereof. Additionally, the implant 2410 is similar, for example, to implant 1910 in that the elongate members 2472, 2474 are broad at the proximal ends thereof (e.g., each elongate member 2472, 2474 includes a wide loop 2442a,b at the distal end to form openings 2495a,b therein). The elongate members 2472, 2474 can form a narrow neck 2424 of the implant 2410 between the loops 2442a,b and the junction 2470. The junction 2470 can act as a pivot for the two elongate members 2472, 2474 such that the elongate members 2472, 2474 can move towards one another (or even over one another) when compressed. Because the elongate members 2472, 2474 are disconnected at the proximal ends, the members 2472, 2474 can flex with respect to one another to allow for conformation with the nasal anatomy. Additionally, the loops 2442a,b can provide flexibility at discrete locations for conformation to the nasal anatomy. The implant 2410 can be, for example, 0.8 mm-1.2 mm, such as 1.0 mm thick. FIG. 25 shows an implant 2510 that is similar to implant 2410 except that it is thinner (e.g., less than 1 mm). Additionally, the neck 2524 is broader (e.g., bows outwards relative to the junction 2570 rather than inwards).

Figure 26:
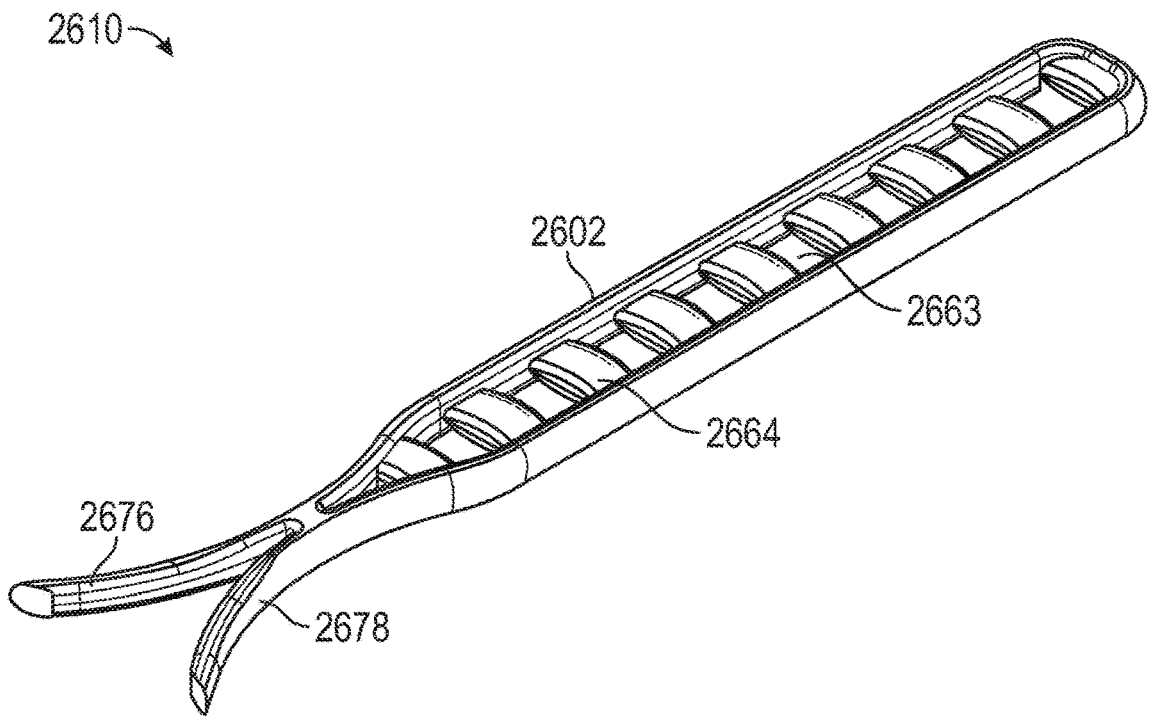
FIG. 26 shows an exemplary nasal implant.
Figure 27:
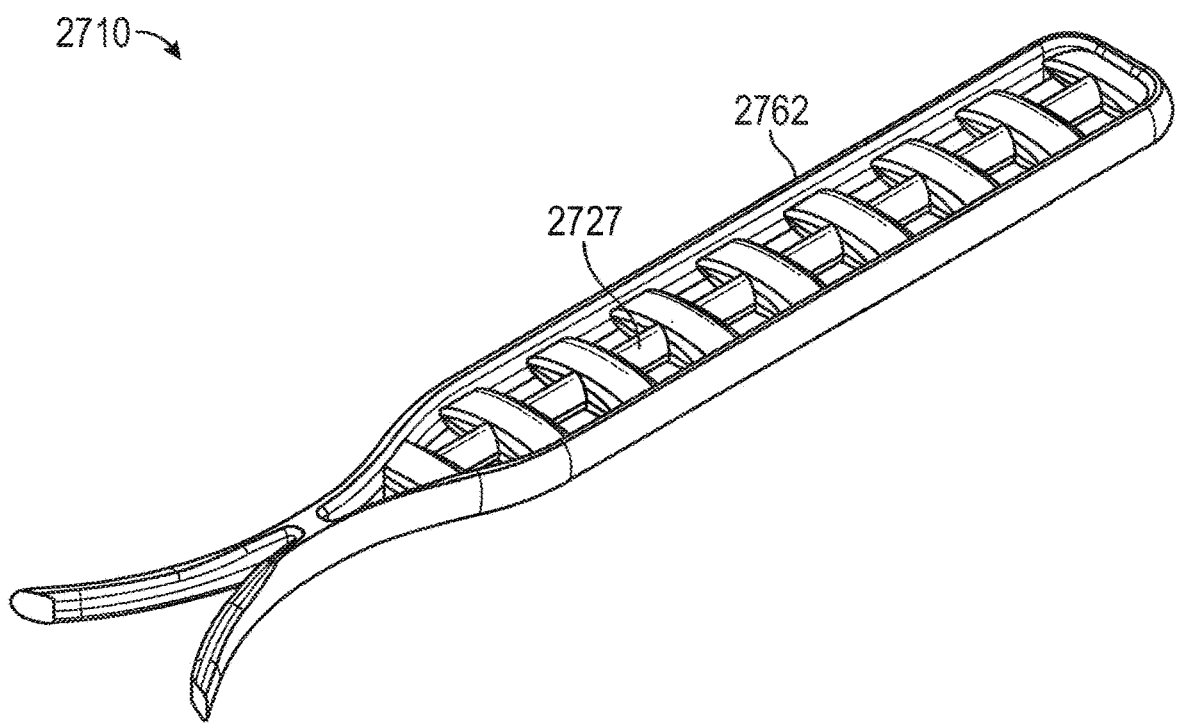
FIG. 27 shows an exemplary nasal implant.

FIGS. 26-27 show additional exemplary implants 2610, 2710 that that can be flexible at discrete locations, compressible in at least one direction, and provide a rigid backstop to deformation of the nasal anatomy. FIG. 26 shows an implant 2610 having wide elongate body 2662. The elongate body 2662 includes a plurality of rib members 2664 extending laterally therethrough and separated by openings 2663. The rib members 2664 and openings 2663 can provide flexibility at discrete locations upon implantation to allow for conformation to the nasal anatomy. The implant additional includes two barbs 2676, 2678 at the distal end thereof. The thickness of the implant 2610 can be, for example, less than 1 mm. FIG. 27 shows an implant 2710 that is similar to implant 2610, but includes a longitudinal 2727 extending down the center of the wide elongate body 2762.

Figure 28A:
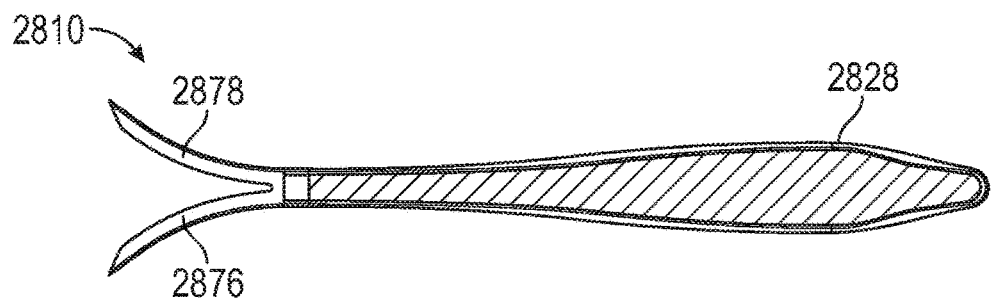
FIGS. 28A-28B show exemplary nasal implants.
Figure 28B:
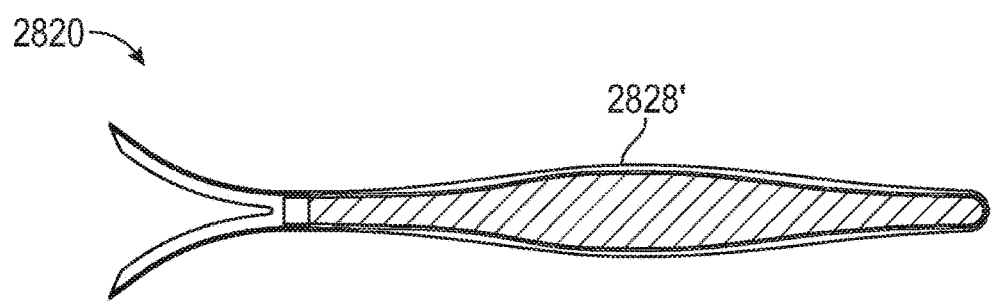

FIGS. 28A-28B show additional implants 2810, 2820 that that can be flexible at discrete locations and provide a rigid backstop to deformation of the nasal anatomy. FIG. 28A shows an implant 2810 having an elongate body that has a wide central portion 2828 and tapers near the proximal and distal ends. The implant 2810 further includes two parts 2876, 2878 at the distal end of the implant 2810. Implant 2810 has the wider portion 2828 in a proximal position to support a caudal area of the nose. In contrast, referring to FIG. 28B, implant 2820 has the wider portion 2828' in a more central or distal position so as to support an area closer to the nasal bone. The implants 2810, 2820 can be flexible at discrete locations along the longitudinal axis so as to conform to the nasal anatomy while providing stiffness in the transverse axis.

Figure 30:
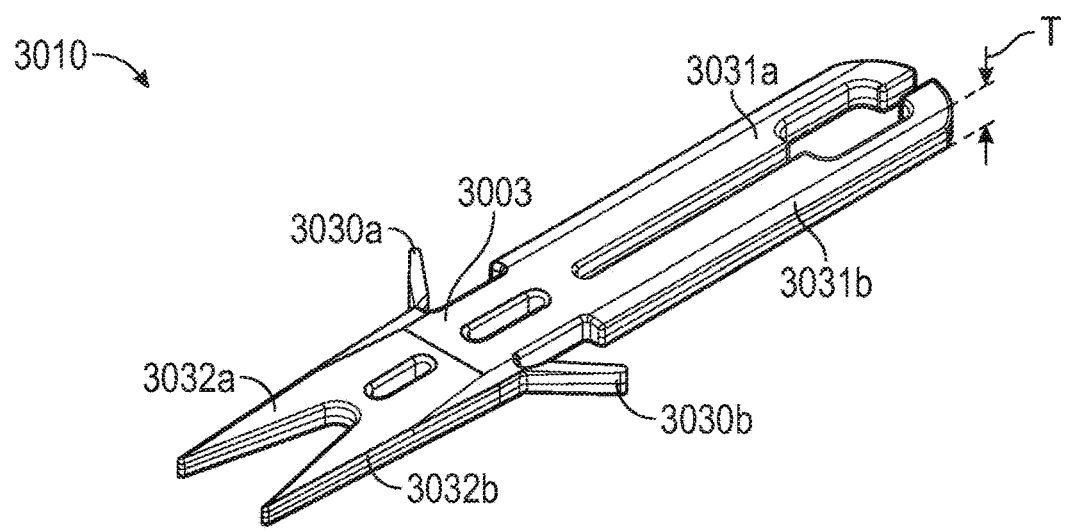
FIG. 30 shows an exemplary nasal implant.

FIG. 30 shows another exemplary implant 3010 that can be flexible at discrete locations and provide a rigid backstop to deformation of the nasal anatomy. The implant 3010 has a generally flat profile with two pointed forks 3032a,b at the distal end and elongated legs 3031a, b at the proximal end. Side barbs 3030a,b extend from a thick neck 3003 in the plane of the implant 3010. Holes 3004 can be positioned along the longitudinal axis to provide tunable rigidity and facilitate blood flow around the nasal tissues within the lateral wall. In some embodiments, the implant 3010 can have a thickness T of 0.5-0.8 mm. The legs 3031a,b can be configured to compress together and/or the barbs can be configured to move inwards in order to collapse the implant 3010 during delivery.

Figure 35:
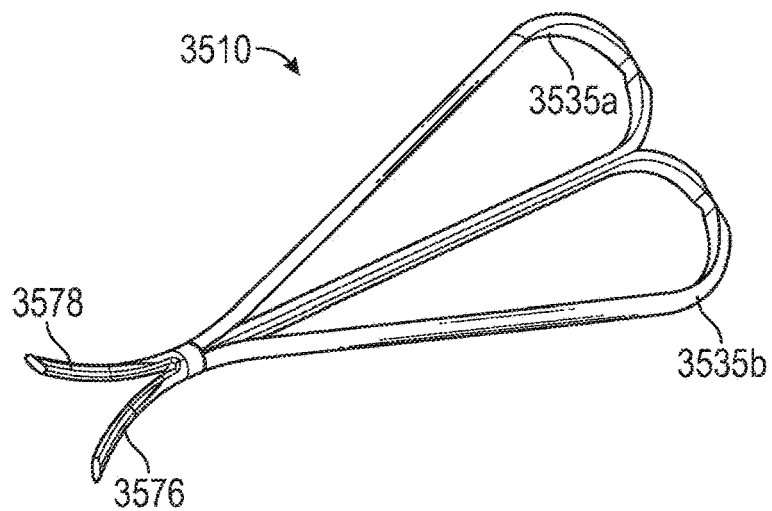
FIG. 35 shows an exemplary nasal implant.
Figure 36:
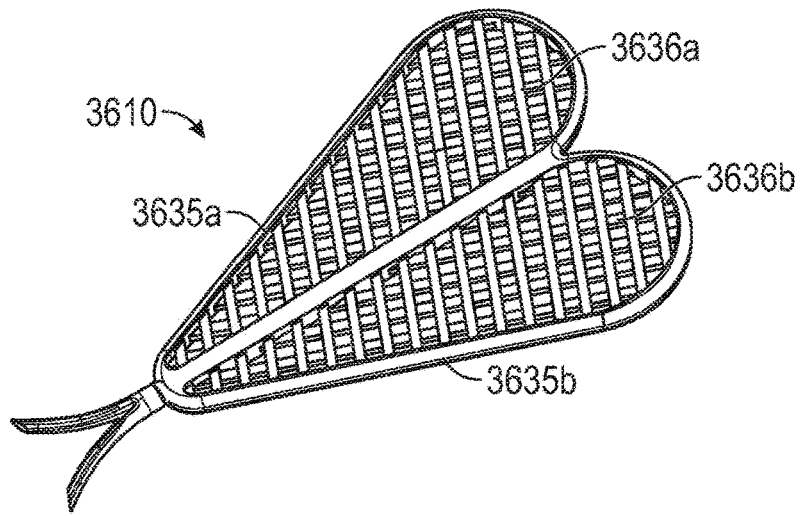
FIG. 36 shows an exemplary nasal implant.

FIGS. 35-36 show additional exemplary implants 3510, 3610 that can be flexible at discrete locations, compressible in at least one direction, and provide a rigid backstop to deformation of the nasal anatomy. Referring to FIG. 35, the implant 3510 includes two looped proximal extensions 3535a,b and two distal barbs 3576, 3578 all extending within a single plane (i.e., the implant has a flat profile). The looped proximal extensions 3535a,b can be open in the center so as to compress when the extensions 3535a,b are pushed towards one another. In some embodiments, the implant 3510 can include a living hinge feature at the proximal end thereof to allow the implant 3510 to compress even further. FIG. 36 shows an implant 3610 that is similar to implant 3510 except that it includes a mesh or perforated material 3636a,b within each of the looped proximal extensions 3635a,b.

Figure 38:
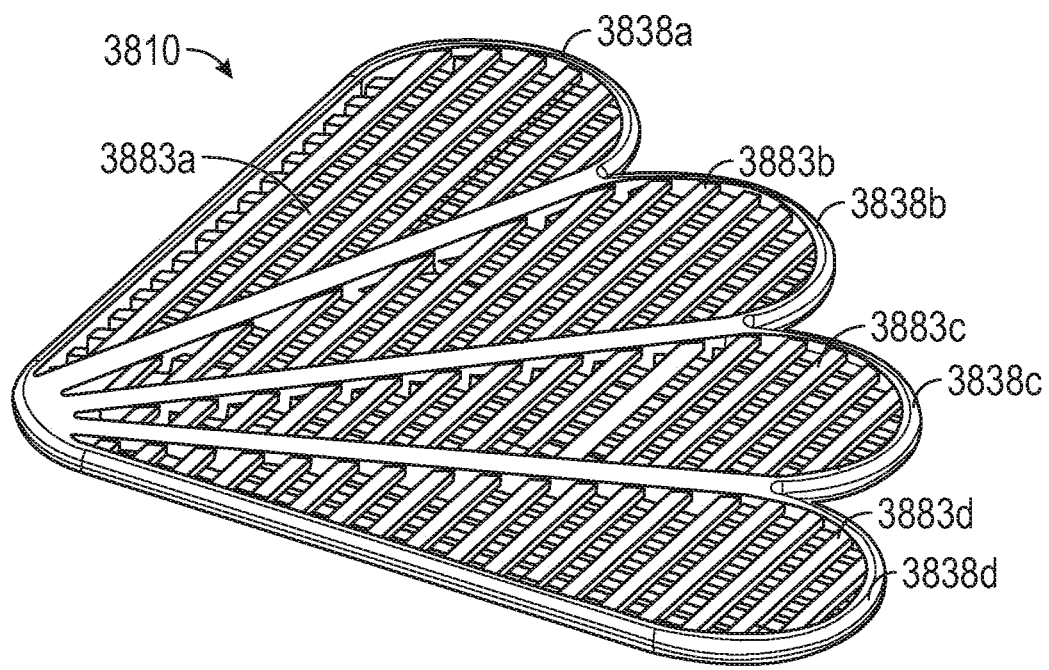
FIG. 38 shows an exemplary nasal implant.
Figure 39:
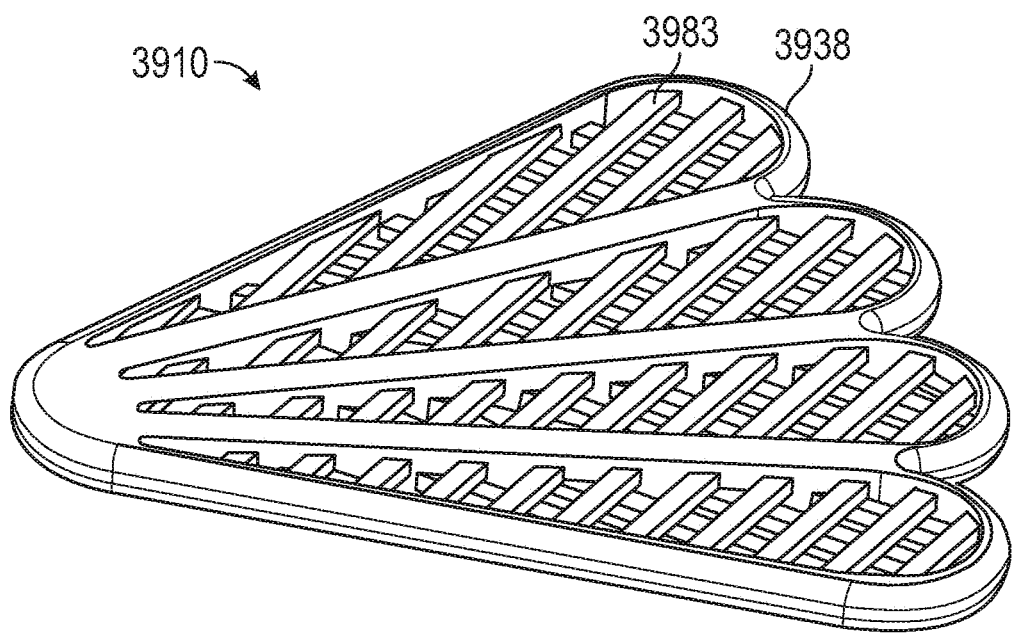
FIG. 39 shows an exemplary nasal implant.
Figure 40:
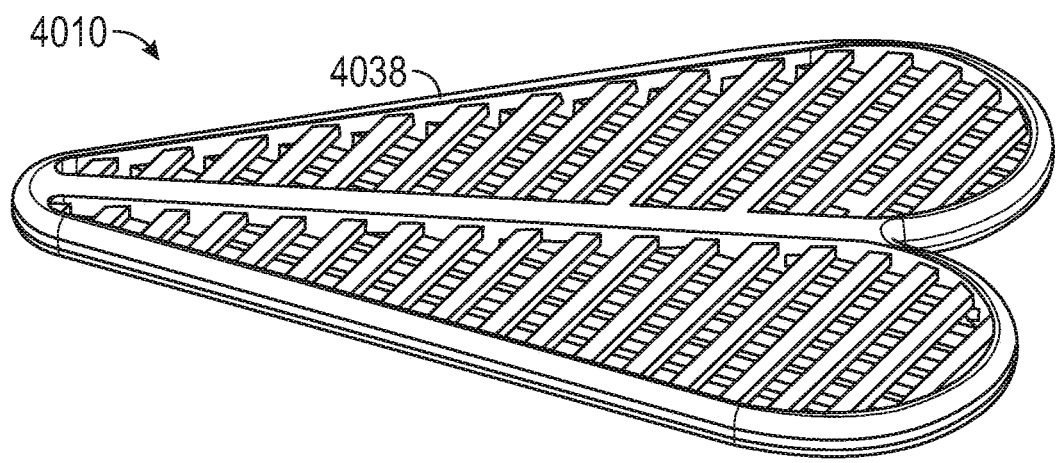
FIG. 40 shows an exemplary nasal implant.

FIGS. 38-40 show additional exemplary implants 3810, 3910, 4010 that can be flexible at discrete locations, compressible in at least one direction, and provide a rigid backstop to deformation of the nasal anatomy. FIG. 38 shows an implant 3810 having three tear-drop shaped sections 3838a,b,c,d side-by-side (e.g., extending across an angle of approximately 90 degrees). The sections 3838a,b, c,d can have a mesh or perforated material 3883a,b,c,d therein. The mesh material 3883a,b,c,d advantageously allows the implant 3810 to compress (e.g., such that the sections 3838a,b,c,d draw closer together). The mesh material 3883a,b,c,d can also allow the implant 3810 to flex at discrete locations while still providing resistance to collapse when a force is applied across the entire implant 3810. The implant 3910 of FIG. 39 is similar to implant 3810 except that the mesh 3983 in each section 3938 includes wider apertures or perforations. The implant 4010 of FIG. 40 is similar to implant 3810 except that it includes only two sections 4038 and extends across an angle of approximately 45 degrees.

Figure 41:
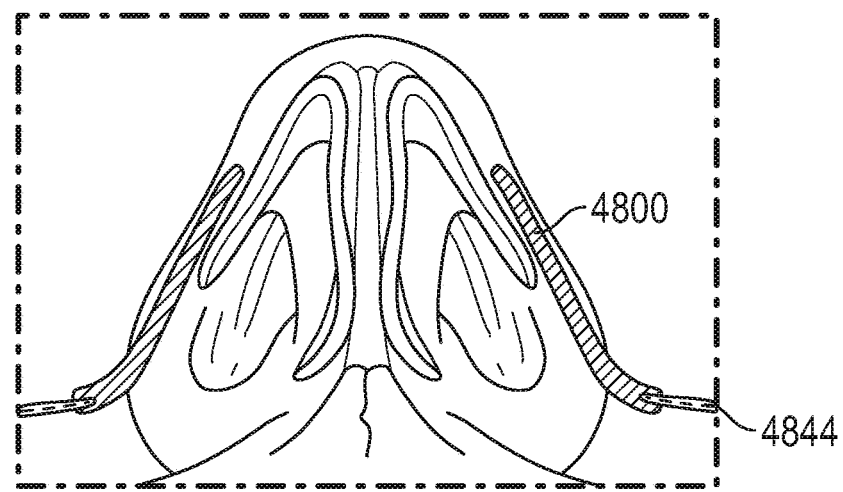
FIG. 41 shows exemplary placement of distal fork features within the nasal anatomy.
Figure 44A:
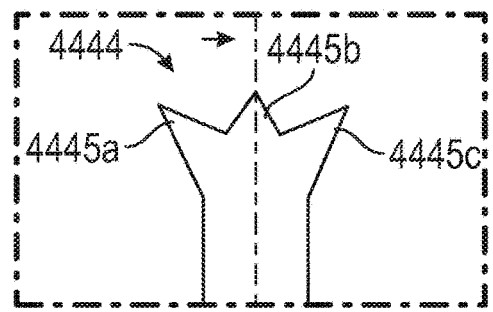
FIGS. 44A-44B shows exemplary distal fork features for a nasal implant.
Figure 44B:
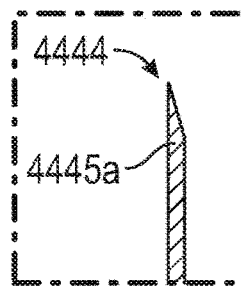
Figure 45A:
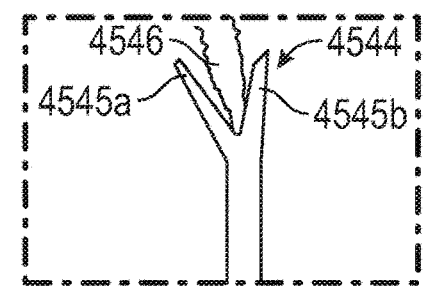
FIGS. 45A-45B shows additional exemplary distal fork features for a nasal implant.
Figure 45B:
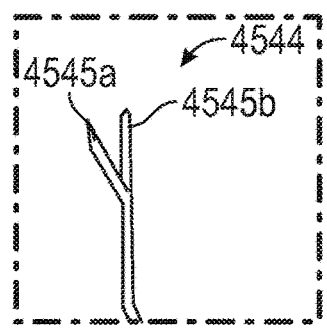
Figure 46:
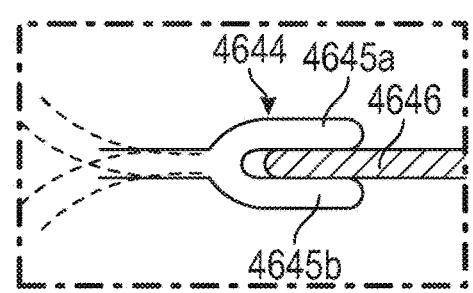
FIG. 46 shows additional exemplary distal fork features for a nasal implant.
Figure 47A:
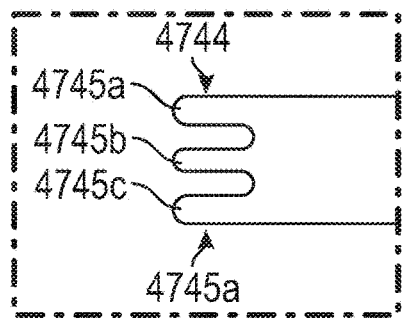
FIGS. 47A-47B shows additional exemplary distal fork features for a nasal implant.
Figure 47B:
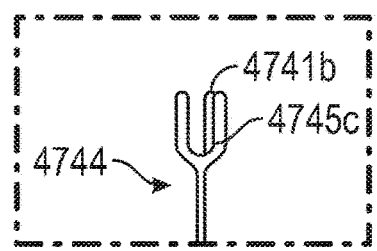

Any of the implants described herein can include fork or barbed features on the distal ends thereof for engagement with the nasal anatomy. For example, referring to FIGS. 44A-44B, the distal end 4444 of an implant can include three sharp forks or barbs 4445a,b,c extending therefrom. The sharp tips of the barbs 4445a,b,c can be configured, for example, to dig into the periosteum when implanted. FIGS. 45A-45B show another exemplary distal end 4544 of an implant that includes two sharp forks or barbs 4544a,b. The distal end 4544 can be configured to bottom out against the bone 4546 (e.g., the maxilla/nasal bone). FIG. 46 shows another exemplary distal end 4644 of an implant with two atraumatic fork features 4645a,b configured to be positioned around bone 4646. FIGS. 47A-47B show another exemplary distal end 4644 of an implant. The distal end includes three off-center fork features 4645a,b,c that can be positioned around bone. The positioning of implant 4800, which can include any of the distal ends 4444, 4544, 4644, 4744) is shown in FIG. 41 with the distal forked feature extending around the bone 4844 (e.g., the maxilla/nasal bone).

It is to be understood that any of the features of described herein with respect to one embodiment herein can be substituted or combined with any of the features described herein with respect to any other embodiment. Additionally, it is to be understood that the relative placement of implants described herein with respect to one implant embodiment can be used for any other embodiment described herein.

Figure 10A:
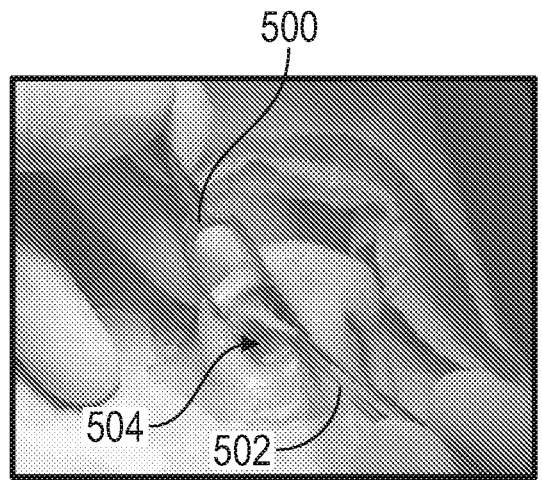
FIGS. 10A-10D illustrate various steps for placing a nasal implant within nasal tissue of a patient.
Figure 10B:
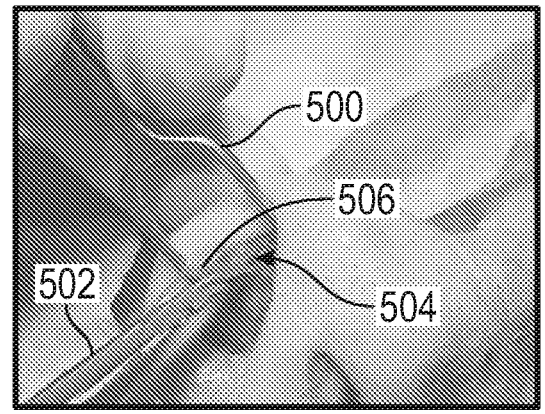
Figure 10C:
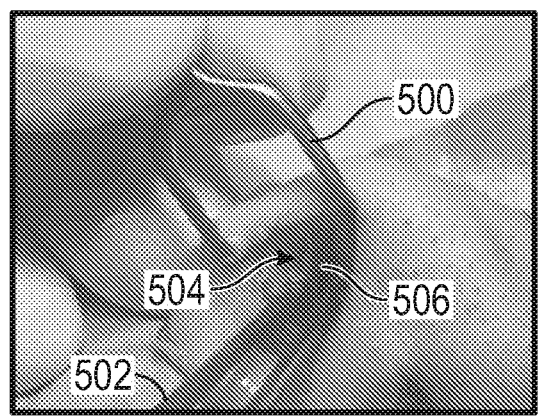
Figure 10D:
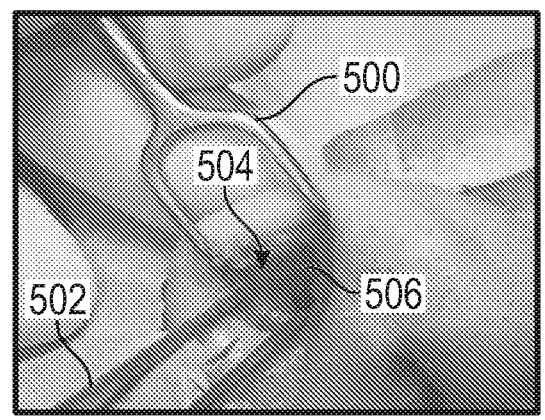

FIGS. 10A-10D illustrate exemplary steps for placing a nasal implant as described herein. The steps illustrated in FIGS. 10A-10D are more invasive than a minimally invasive procedure (e.g., where the implant would be delivered with a needle), but less invasive than open surgical techniques that are used to deliver nasal implants (e.g., surgical delivery of batten grafts and spreader grafts). FIGS. 10A-10B illustrate that a pocket 504 can be formed within the nasal tissue. Forceps 500 and tweezers 502 can then be used to place the nasal implant 506 (which can be any implant described herein) within the pocket 504. FIG. 10C shows the tweezers 502 being used to orient the nasal implant 506 within the pocket 504. FIG. 10D shows the nasal implant 506 within the pocket 504 in the desired orientation. After placing the implant 506, the forceps 500 and tweezers 502 can be removed from the nasal tissue. In some cases, the nasal tissue can be sutured to close the pocket. In addition to or instead of using the forceps 500 and tweezers 502, a delivery tool as described herein can be used to place the nasal implant in the pocket within the nasal tissue. In some embodiments, the nasal implant can be carried to the pocket in a compressed or partially compressed state within the delivery tool. In some cases, the delivery tool can have a sharpened surface to partially form or enlarge the pocket in the nasal tissue or to make access to the nasal pocket easier.

Figure 16:
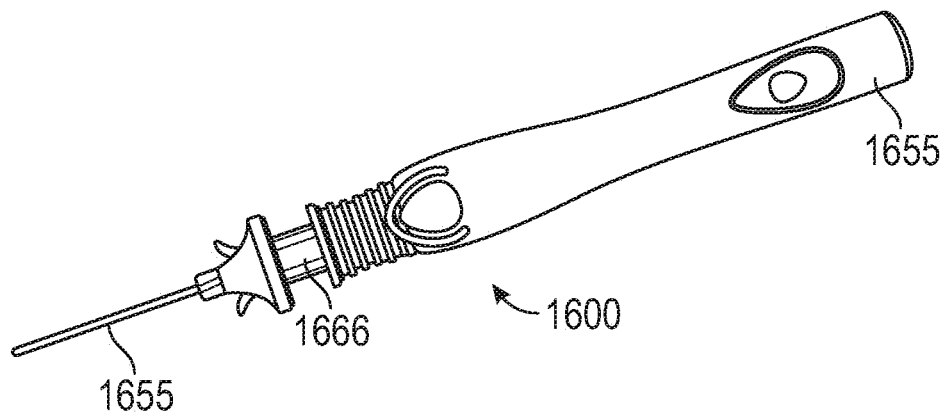
FIG. 16 illustrates an exemplary delivery tool that can be used to deliver the implants described herein.
Figure 29A:
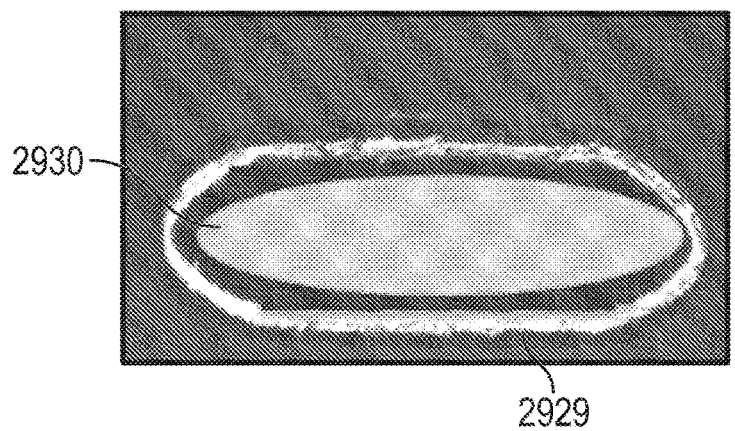
FIGS. 29A-29D show cross-sections of an exemplary delivery device cannulas.
Figure 29B:
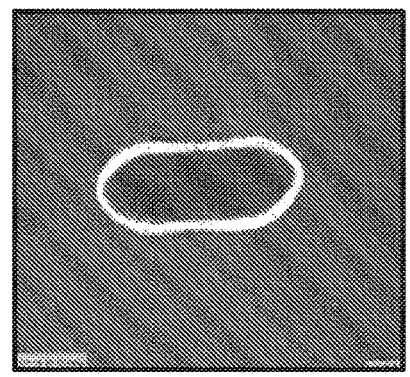
Figure 29C:
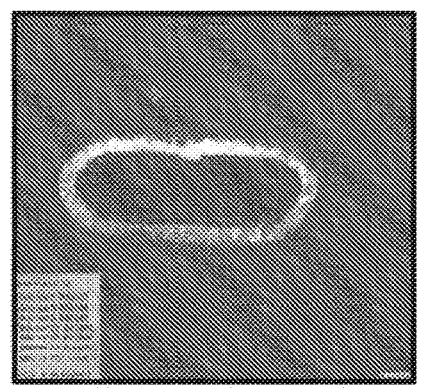
Figure 29D:
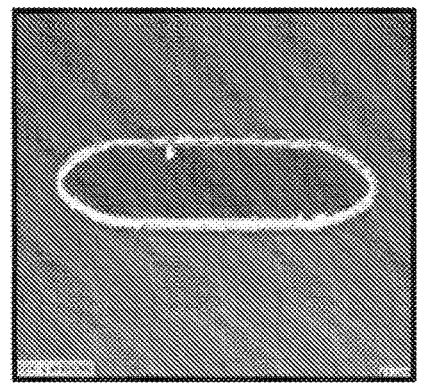

FIG. 16 shows an exemplary delivery tool 1600 that can be used to deliver an implant as described herein. The delivery tool 1600 includes a handle 1655 that is moveable with respect to an inner portion 1666 and a needle 1665 configured to allow for the passage of the implant therethrough Delivery tool features are described in International Application No. PCT/US18/24932, filed Mar. 28, 2018, titled "NASAL DELIVERY TOOLS, SYSTEMS, AND METHODS OF USE", the entirety of which is incorporated by reference herein. The needle can have a relatively large diameter (e.g., greater than 16 gauge) and/or an oval perimeter in order to allow for the passage of the implants described herein therethrough. An exemplary flattened or oval delivery device cannula cross section 2929 with an implant cross section 2930 is shown in FIG. 29A. Additional exemplary flattened or oval cannula cross sections are shown in FIGS. 29B-29D.

Figure 11A:
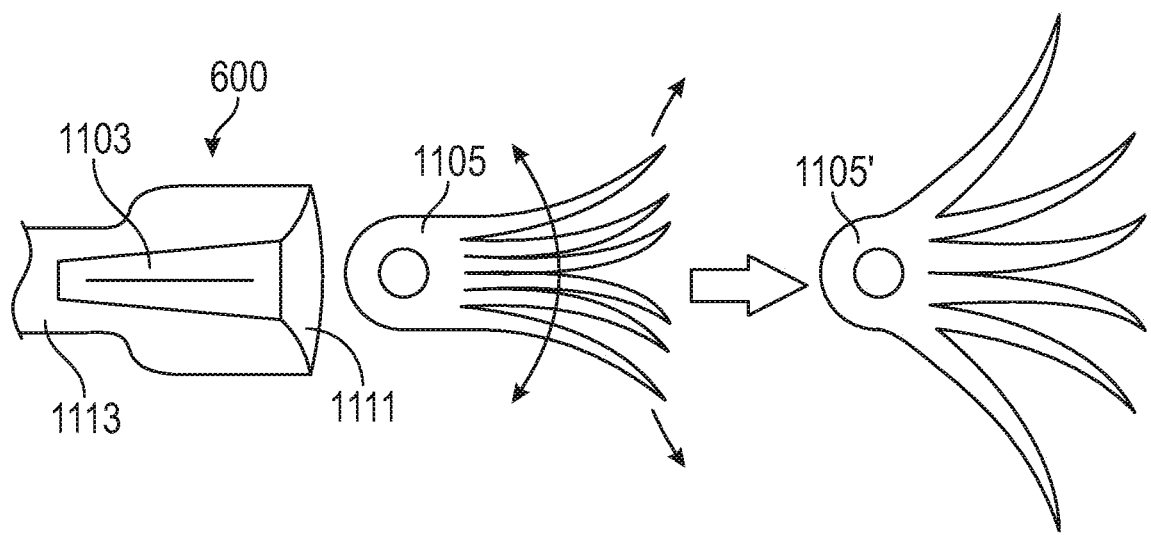
FIGS. 11A-11B illustrate exemplary delivery tools that can be used to deliver the implants described herein.
Figure 11B:
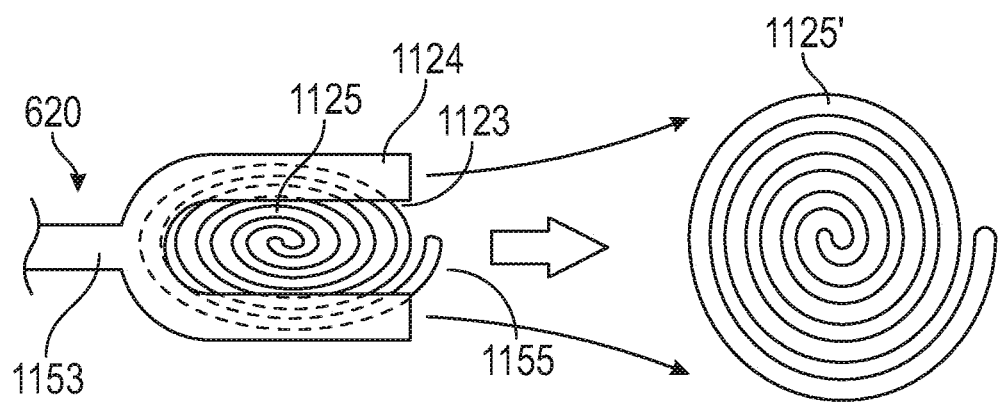

FIGS. 11A-11B illustrate exemplary of embodiments of delivery tools 600, 620 that can be used to deliver the implants descried herein. The delivery tool 600 shown in FIG. 11A includes a compartment 1103 for carrying the nasal implant 1105 in a compressed configuration. After the nasal implant 1105 is ejected from the compartment 1103, can expands to the expanded configuration (labeled at 1105'). The delivery tool 600 is illustrated with a distal opening 1111 that is in line with the axis of the elongate portion 1113 of the delivery tool 600. The delivery tool 620 shown in FIG. 11B includes a forked distal end 1124 with a compartment 1123 between the forked features for carrying the nasal implant 1125 in a compressed configuration. After the nasal implant 1125 is ejected from the compartment 1123, it can expand to the expanded configuration (labeled as 1125'). The delivery tool 620 is illustrated with an opening 1155 that is in line with the axis of the elongate portion 1153 of the delivery tool. In other implementations the opening can be orthogonal to the axis of the elongate portion or have another orientation relative to the axis of the elongate portion.

Figure 12A:
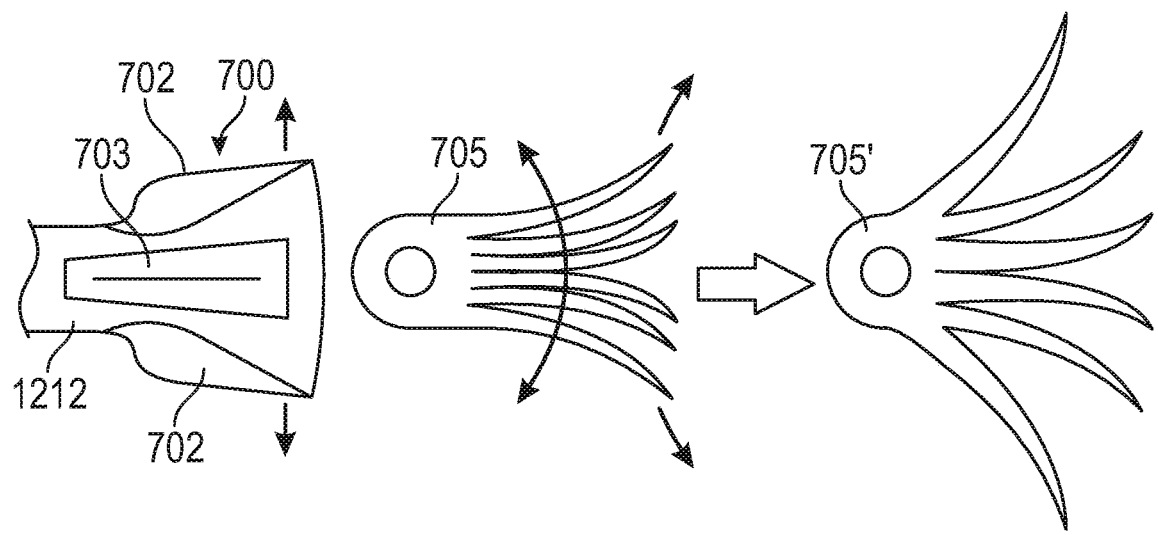
FIGS. 12A-12B illustrate exemplary delivery tools that can be used to deliver the implants described herein.
Figure 12B:
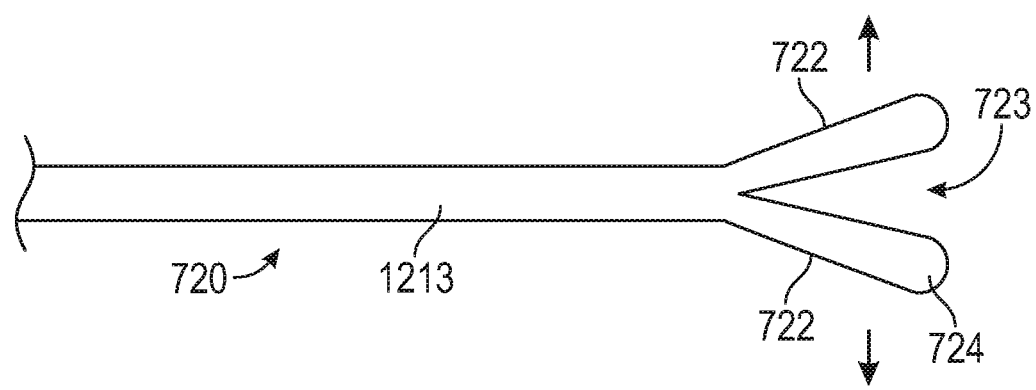

FIGS. 12A-12B illustrate aspects of embodiments of exemplary delivery tools 700, 720 that can be used to deliver the implants described herein. The delivery tool 700 (shown in FIG. 12A) is similar to delivery tool 600 except that it includes cutting surfaces 702 that extend laterally away from a central elongate body 1212 (or central axis) of the tool 700, 720 to cut or separate tissue as the tool 700 is moved through the nasal anatomy. The delivery tool 700, like delivery tool 600, includes a compartment 703 for carrying the nasal implant 705 in a compressed configuration. After the nasal implant is ejected from the compartment 703, it can expand to the expanded configuration (labeled 705'). The delivery tool 720 (shown in FIG. 12B) is similar to tool 620 except that it includes cutting surfaces 722 that extend laterally away from a central elongate body 1213 (or central axis) of the tool 720 to cut or separate tissue. The delivery tool 720, like tool 620, includes a forked distal end 724 with an opening 723 between the forks configured to carry the nasal implant in a compressed configuration.

Figure 22:
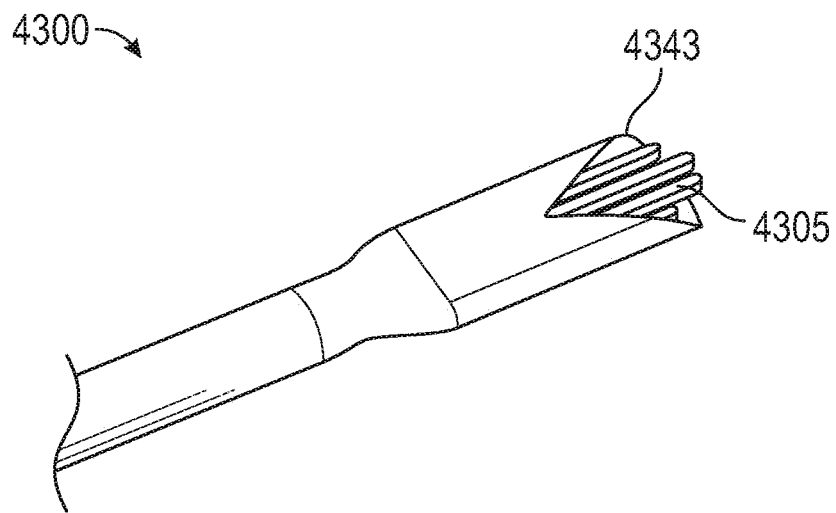
FIG. 22 shows the distal end of an exemplary delivery tool for a nasal implant as described herein.

The distal end of another exemplary delivery tool 4300 is shown in FIG. 22. The distal end is flattened and can include an open compartment 4343 therein configured to hold a collapsed implant 4305 therein.

Figure 15:
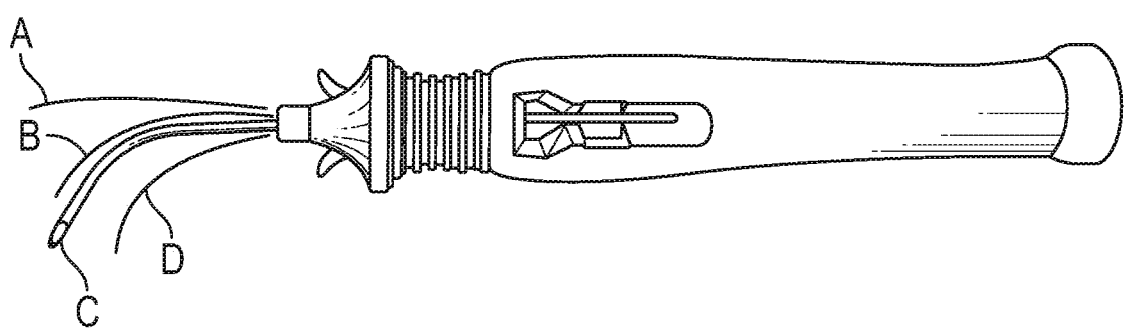
FIG. 15 illustrates flexing of a distal end of a delivery tool.

Referring to FIG. 15, in some embodiments, the distal end 1515 of a delivery tool 1500 can be configured to so as to change angles (differing angles A, B, C, and D are shown in FIG. 15) in order to provide access to various areas of the nasal anatomy and/or to delivery the implant at the desired orientation.

Figure 14:
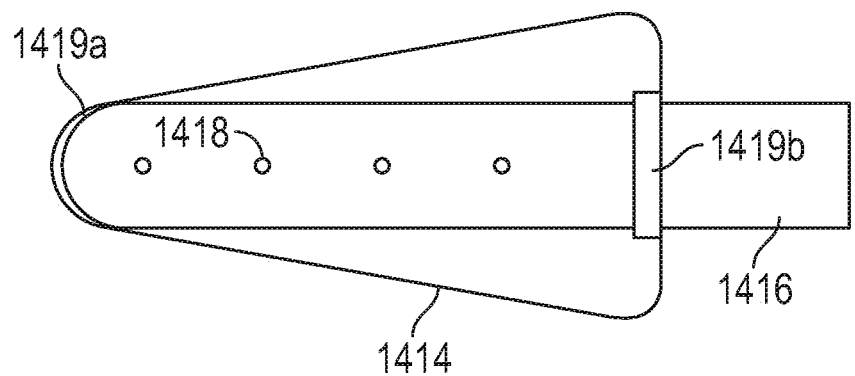
FIG. 14 illustrates an exemplary tool configured to make a pocket in the nasal anatomy.

In some embodiments, a specialized tool can be used to create a pocket in the nasal anatomy for placement of an implant therein. For example, FIG. 14 shows an exemplary tool 1400 for creating a pocket in a nasal wall. The tool 1400 includes a cannula or catheter body 1416 with a balloon 1414 on the distal tip thereof. The balloon 1414 can be tapered from the proximal end to the distal end so as to create a pocket as the balloon 1414 is inflated within the nasal anatomy. The catheter body 1416 can include ports 1418 for supply gas or fluid to inflate the balloon 1414. Further, distal and proximal seals 1419a,b can ensure that the air or fluid in the balloon 1414 does not leak.

Another exemplary tool 1800 for creating a pocket in the nasal wall is shown in FIG. 18. The tool 1800 includes an elongate body 1818. Two reverse blades 1819 can extend laterally from the elongate body 1818 to create a large diameter pocket. The blades 1819 can be configured to extend from and collapse back into the elongate body 1818.

Figure 23A:
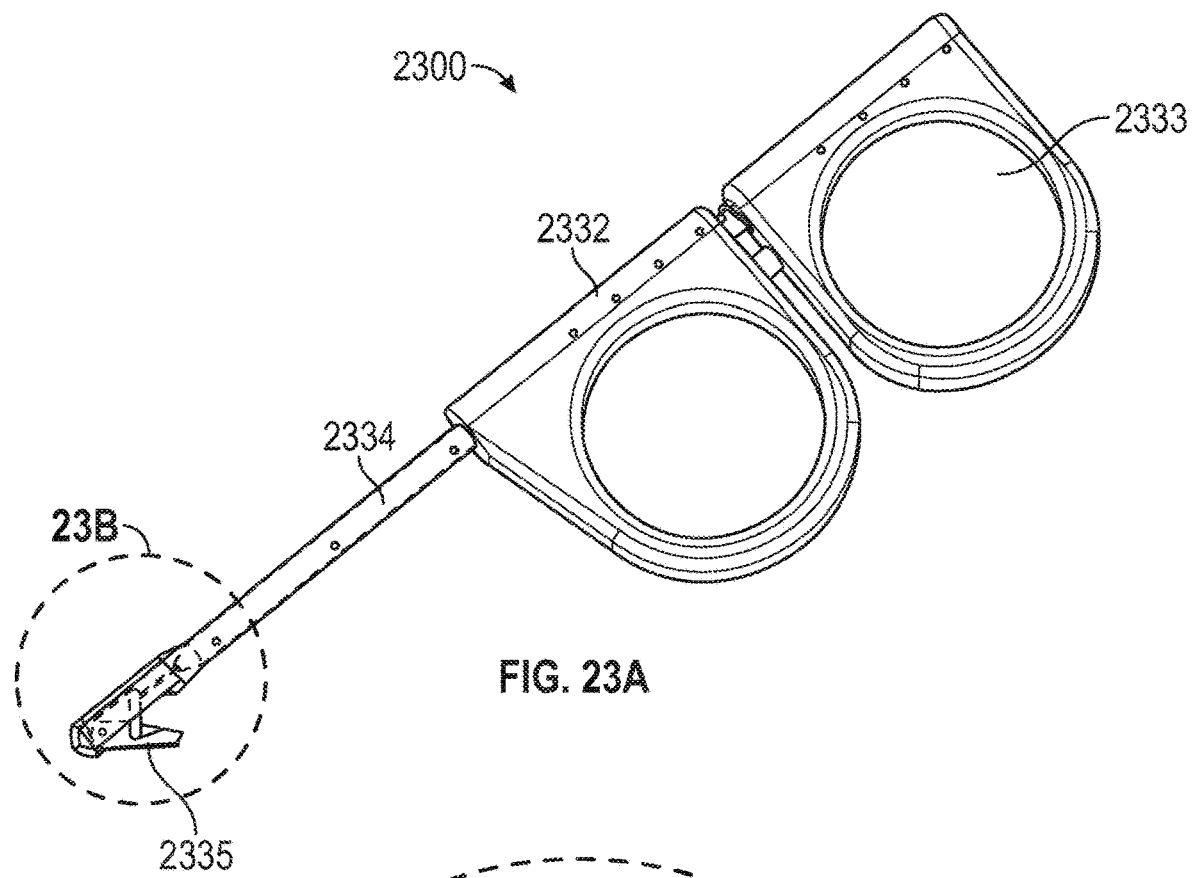
FIGS. 23A-23B shows an exemplary tool configured to make a pocket in the nasal anatomy.
Figure 23B:
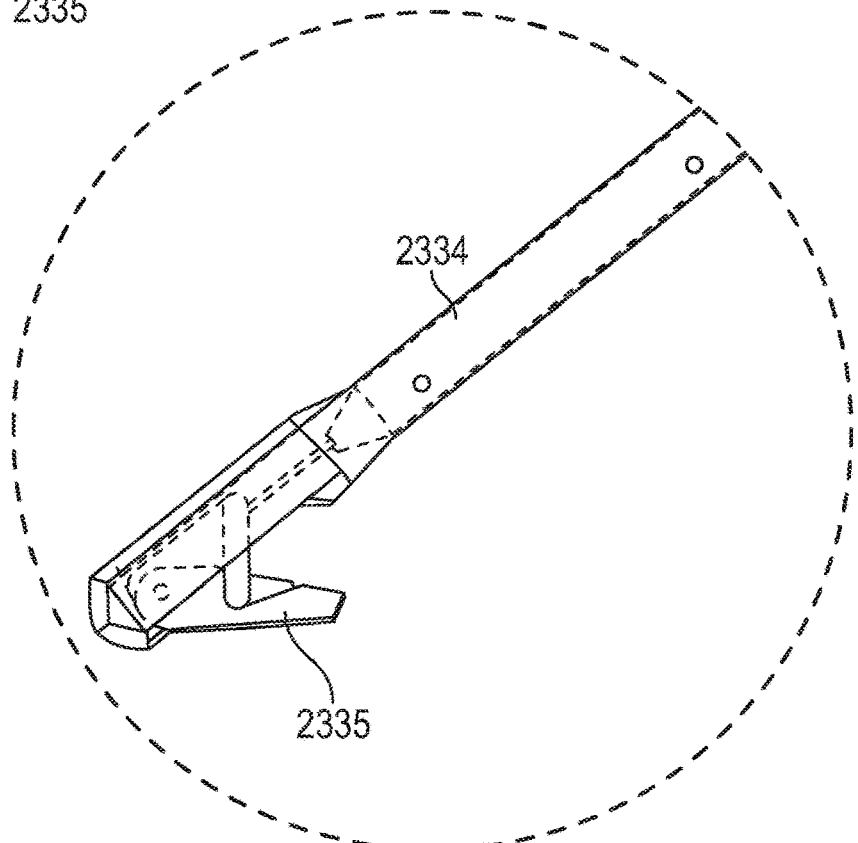

Another exemplary tool 2300 for creating a pocket in the nasal wall is shown in FIGS. 23A-23B. The tool 2300 includes an ergonomic handle 2332 with two holes 2333 for positioning one or more fingers therethrough. The tool 2300 can further include an elongate body 2334 extending from the handle 2332 with an extendable blade 2335 at the distal end thereof. In some embodiments, the blade 2335 can be configured to be extended or deployed using a cam-based deployment system.

Another exemplary tool 3200 for creating a pocket in the nasal wall is shown in FIGS. 32A-32C. The tool 2300 includes a handle 3232 with three extensions 3231a,b,c having central holes 3233a,b,c for positioning one or more fingers therethrough. One of the extensions 3231b (e.g., the middle extension) can be configured to move relative to the other two extensions 3231. The movement of the extension 3231b can activate a blade 3235 at the distal end of the elongate body 3234 to move the blade 3235 from a stowed to an exposed position (e.g., via a spring or cam mechanism). The tool 3200 can advantageously be a singled handed tool that can create a pocket in the lateral wall through only a small incision.

Figure 42A:
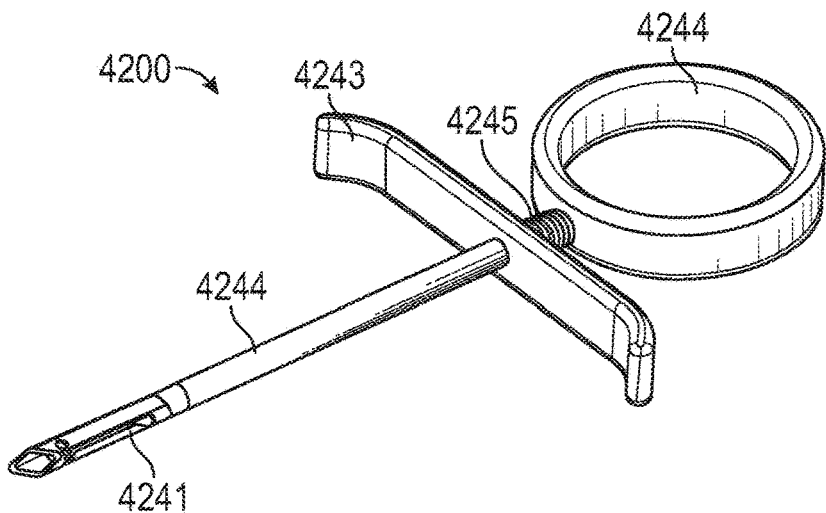
FIGS. 42A-42C show an exemplary tool configured to create a pocket in the nasal anatomy.
Figure 42B:
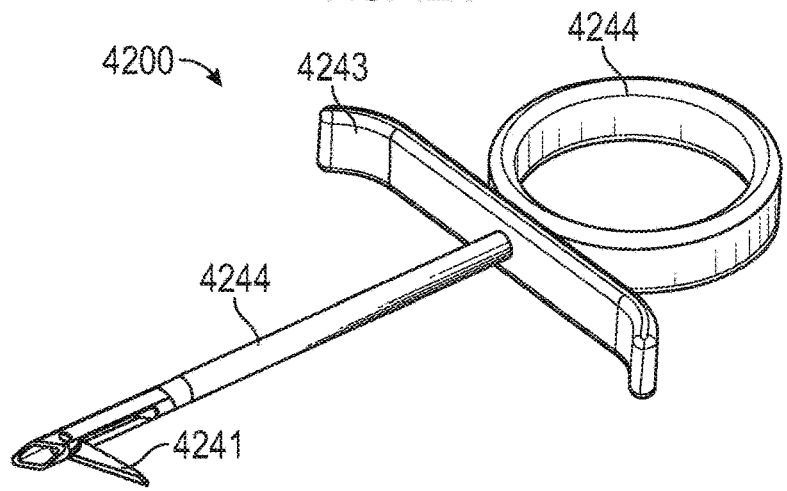
Figure 42C:
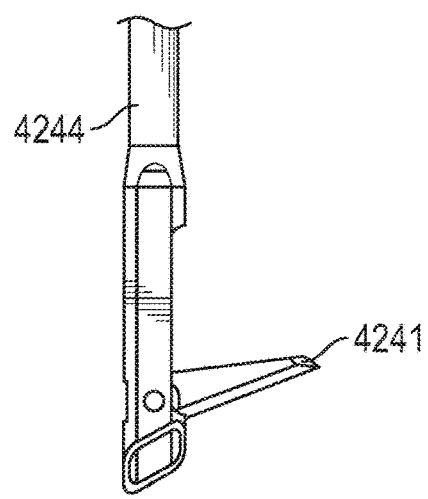

Another exemplary tool 4200 for creating a pocket in the nasal wall is shown in FIGS. 42A-42C. The tool 4200 includes an elongate body 4242, a traverse proximal bar 4243, a circular element 4244, and a spring 4245 between the circular element 4244 and the proximal bar 4243. A blade 4241 can be configured to extend from the distal end of the elongate body 4244. To activate the blade 4241 from the stowed configuration (shown in FIG. 42A) to the deployed configuration (shown in FIG. 42B), the user can push on the circular element 4244 while holding the transverse bar 4243 stationary, thereby compressing the spring 4245 and releasing the blade 4241. The tool 4200 can advantageously be held and activated with a single hand and can create a pocket in the lateral wall through only a small incision.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A nasal implant extending from a proximal end to a distal end; the comprising:
    a plurality of barbs disposed at the distal end of the implant;
    a first elongate member;
    a second elongate member, wherein the first elongate member and the second elongate member together form a profile of the implant at the proximal end of the implant; and
    a junction disposed distally from the first elongate member and the second elongate member,
    wherein the nasal implant is flexible at discrete locations along the profile;
    wherein the nasal implant as a whole is configured to be rigid along the profile when a force is applied to substantially all of the profile; and
    wherein the first elongate member and the second elongate member are connected together at the junction and are disconnected at the proximal end of the implant, the junction providing a pivot for the first elongate member and the second elongate member such that the first elongate member and the second elongate member can move towards one another when compressed.

2. The nasal implant of claim 1, wherein the first elongate member and the second elongate member are substantially equal in size.

3. The nasal implant of claim 1, wherein the first elongate member and the second elongate member are substantially symmetrical.

4. The nasal implant of claim 1, wherein the first elongate member and the second elongate member are substantially straight.

5. The nasal implant of claim 1, wherein the first elongate member and the second elongate member each have a plurality of ridges extending therearound.

6. The nasal implant of claim 1, wherein the implant has a width of 3-5 mm, a height of 3 mm or more, and a thickness of 1 mm or less.

7. The nasal implant of claim 1, where the nasal implant is configured to fit between a mucosa and a dermis of a nasal lateral wall.

8. The nasal implant of claim 1, wherein the nasal implant is configured to fit between the mucosa and a nasal septum.

9. The nasal implant of claim 1, wherein the implant includes at least one open space therein that includes from about 5% to about 20% of a surface area of the profile.

10. The nasal implant of claim 1, wherein the implant includes at least one open space therein that includes about 20% or greater of a surface area of the profile.

11. The nasal implant of claim 1, wherein the profile has a flexural rigidity of about 2 N*mm$^2$ to about 500 N*mm$^2$.

12. The nasal implant of claim 1, wherein the nasal implant comprises a first bioabsorbable material.

13. The nasal implant of claim 12, wherein the nasal implant consists essentially of the first bioabsorbable material.

14. The nasal implant of claim 12, wherein the nasal implant includes the first bioabsorbable material with a first degradation profile and a second bioabsorbable material with a second degradation profile.

15. The nasal implant of claim 14, wherein the first bioabsorbable material is polydioxanone, and wherein the second bioabsorbable material is selected from the group consisting of: PLA, PLLA, and PLDLA.

16. The nasal implant of claim 14, wherein the first degradation profile is about 1 to 6 months, and wherein the second degradation profile is about 18 to 48 months.

* * * * *